US012383158B2

United States Patent
Stocker et al.

(10) Patent No.: US 12,383,158 B2
(45) Date of Patent: Aug. 12, 2025

(54) DETECTION OF HIGH-RISK UNSTABLE ATHEROSCLEROTIC PLAQUE

(71) Applicant: The Heart Research Institute Ltd, Newtown (AU)

(72) Inventors: Roland Stocker, Sydney (AU); Imran Rashid, Sydney (AU)

(73) Assignee: The Heart Research Institute Ltd, Newtown (AU)

( * ) Notice: Subject to any disclaimer, the term of this patent is extended or adjusted under 35 U.S.C. 154(b) by 0 days.

(21) Appl. No.: 18/408,961

(22) Filed: Jan. 10, 2024

(65) Prior Publication Data

US 2024/0138701 A1    May 2, 2024

Related U.S. Application Data

(63) Continuation of application No. 17/262,457, filed as application No. PCT/AU2019/050788 on Jul. 25, 2019, now abandoned.

(30) Foreign Application Priority Data

Jul. 25, 2018    (AU) ................. 2018902699

(51) Int. Cl.
*A61B 5/00*    (2006.01)
*A61B 5/02*    (2006.01)
(Continued)

(52) U.S. Cl.
CPC .......... *A61B 5/055* (2013.01); *A61B 5/02007* (2013.01); *A61B 5/026* (2013.01);
(Continued)

(58) Field of Classification Search
CPC ...... A61B 5/055; A61B 5/02007; A61B 5/026
See application file for complete search history.

(56) References Cited

U.S. PATENT DOCUMENTS

2005/0043614 A1* 2/2005 Huizenga ........... A61B 5/02007
                                                    600/427
2007/0232883 A1* 10/2007 Ilegbusi ................ A61B 5/061
                                                    600/407
(Continued)

FOREIGN PATENT DOCUMENTS

WO    WO 2005/112759 A1    12/2005
WO    WO 2006/014530 A2    2/2006

OTHER PUBLICATIONS

Teng et al., "The Roles of Myeloperoxidase in Coronary Artery Disease and its Potential Implication in Plaque Rupture" Rodox Report, 2017, vol. 22(2), pp. 51-73.
(Continued)

*Primary Examiner* — Joel F Brutus
(74) *Attorney, Agent, or Firm* — BakerHostetler

(57) ABSTRACT

The technology relates to a method for detecting high-risk unstable atherosclerotic plaque in a subject, the method comprising: a) administering to the subject a magnetic resonance imaging (MRI) contrast agent capable of being activated by myeloperoxidase (MPO) in atherosclerotic plaque; b) allowing the contrast agent to be activated by myeloperoxidase in atherosclerotic plaque; c) obtaining an image of the atherosclerotic plaque from the subject using such molecular MRI, wherein enhanced imaging is indicative of unstable plaque. In some embodiments an MPO inhibitor is administered to a subject identified as having a high-risk unstable atherosclerotic plaque.

15 Claims, 22 Drawing Sheets

(51) Int. Cl.
  A61B 5/026    (2006.01)
  A61B 5/055    (2006.01)
  A61K 49/00    (2006.01)
  A61K 49/08    (2006.01)
  A61K 49/10    (2006.01)
(52) U.S. Cl.
  CPC ........ *A61B 5/7275* (2013.01); *A61K 49/0002* (2013.01); *A61K 49/085* (2013.01); *A61K 49/105* (2013.01)

(56) References Cited

U.S. PATENT DOCUMENTS

| | | | |
|---|---|---|---|
| 2008/0044827 A1* | 2/2008 | Bogdanov | G01N 33/5088 435/7.1 |
| 2013/0045161 A1 | 2/2013 | Sigalov | |
| 2018/0078519 A1 | 3/2018 | Van Dyke et al. | |
| 2019/0000846 A1 | 1/2019 | Van Deursen et al. | |

OTHER PUBLICATIONS

Wildgruber et al., "Molecular Imaging of Inflammation in Atherosclerosis", Theranostics, 2013, vol. 3(11), pp. 865-884.
Rodriguez E. et al., "Activatable magnetic resonance imaging agents for myeloperoxidase sensing: mechanism of activation, stability and toxicity", J Am Chem Soc, Jan. 2010; vol. 132, pp. 168-177.
Shazeeb et al., "A Novel Paramagnetic Substrate for Detecting Myeloperoxidase Activity In Vivo", Molecular Imaging, Sep.-Oct. 2012, vol. 11, pp. 433 443.
Ruggeri et al., "Discovery of 2-(6-(5-Chloro-2-methoxyphenyl)-4-oxo-2-thioxo-3,4-dihydropyrimidin-1(2H)-yl) acetamide (PF-06282999): A Highly Selective Mechanism-Based Myeloperoxidase Inhibitor for the Treatment of Cardiovascular Diseases", Journal of Medicinal Chemistry, 2015, vol. 58, pp. 8513-8528.
Zeng et al., "PF-1355, a Mechanism-Based Myeloperoxidase Inhibitor, Prevents Immune Complex Vasculitis and Anti-Glomerular Basement Membrane Glomerulonephritis", Journal of Pharmacology and Experimental Therapeutics, May 2015, vol. 353, pp. 288-298.
Talib et al, "Detailed protocol to assess in vivo and ex vivo myeloperoxidase activity in mouse models of vascular inflammation and disease using hydroethidine", Free Radical Biology and Medicine, 2016, vol. 97, pp. 124-135.
Chen et al., "A Novel Mouse Model of Atherosclerotic Plaque Instability for Drug Testing and Mechanistic/Therapeutic Discoveries Using Gene and MicroRNA Expression Profiling", Circulation Research; 2013; vol. 113, pp. 252-265.
Witting et al., "Site-Specific Antiatherogenic Effect of Probucol in Apolipoprotein E-Deficient Mice", Arteriosclerosis, Thrombosis, and Vascular Biology, Aug. 2000, vol. 20, pp. e26-e33.
Rodriguez et al., "Activatable Magnetic Resonance Imaging Agents for Myeloperoxidase Sensing: Mechanism of Activation, Stability, and Toxicity", Journal of the American Chemical Society, 2010, vol. 132, pp. 168-177 (Abstract Only).
Tiden et al., "2-Thioxanthines Are Mechanism-based Inactivators of Myeloperoxidase That Block Oxidative Stress during Inflammation", Journal of Biological Chemistry, Oct. 2011, vol. 286, pp. 37578-37589.
International Patent Application No. PCT/AU2019/050788, Int'l Written Opinion and Search Report, dated Sep. 25, 2019, 8 pages.
European Patent Application No. 19841196.9; Extended Search Report; dated Mar. 30, 2022; 9 pages.
Rashid et al.; "Molecular Magnetic Resonance Imaging of Vascular Myeloperoxidase Activity for the Identification of Unstable Atherosclerotic Plaque"; Proc. Int'l Soc. of Mag. Reason. Med.; vol. 2776; Apr. 2017; 2 pages (Abstract Only).
Rashid et al.; "Abstract 17662: Myeloperoxidase is a Potential Molecular Imaging and Therapeutic Target for the Identification and Stabilization of Unstable Atherosclerotic Plaque"; Circulation; vol. 136; Jun. 2018; 5 pages (Abstract Only).
Ronald et al.; "Enzyme-Sensitive MR Imaging Targeting Myeloperoxidase Identifies Active Inflammation in Experimental Rabbit Atherosclerotic Plaques"; Circulation; vol. 120(7) Aug. 2009; p. 592-599.
G. Getz; "Mouse Model of Unstable Atherosclerotic Plaque?"; Arterioscler Throm Vasc Biol.; vol. 20; 2000; p. 2503-2505.

* cited by examiner

D

A

B

A

B

A

B

A

B

C

D

E

F

G

H

DETECTION OF HIGH-RISK UNSTABLE ATHEROSCLEROTIC PLAQUE

CROSS-REFERENCE TO RELATED APPLICATIONS

This application is a continuation of U.S. patent application Ser. No. 17/262,457, filed Jan. 22, 2021, which is the National Stage of International Patent Application No. PCT/AU2019/050788, filed Jul. 25, 2019, which claims the benefit of Australian Patent Application No. 2018902699, filed Jul. 25, 2018, the disclosures of which are incorporated herein by reference in their entireties.

TECHNICAL FIELD

The technology relates to the role of myeloperoxidase (MPO) as diagnostic for high-risk (unstable) atherosclerotic plaque. More particularly, the technology relates to non-invasive molecular magnetic resonance imaging (MRI) methods using MPO-activated contrast agents for the in vivo detection of unstable atherosclerotic plaques. The methods may be used for the diagnosis of subjects at risk of developing inflammation (including vascular inflammation) or an acute cardiovascular event.

BACKGROUND

The rupture of high-risk vulnerable or unstable atherosclerotic plaque is the initiating event for the majority of myocardial infarctions. Culprit lesions are characterised by thin fibrous caps, high inflammatory cell content and lipid-rich necrotic cores. Inflammation is a key driver of plaque rupture as it enhances collagen degradation and impairs fibrous cap formation. Myeloperoxidase (MPO) is an inflammatory enzyme abundantly expressed in culprit coronary plaque in fatal cases of acute myocardial infarction.

Furthermore, circulating concentrations of MPO predict major adverse cardiac events in patients presenting with chest pain and in the post-infarct setting. Possible mechanistic links between MPO and plaque instability include induction of endothelial cell apoptosis, activation of latent proteinases, and the promotion of pro-coagulant and pro-thrombotic effects. However, despite its involvement in numerous pathological pathways and its strong association with major adverse cardiac events, a causal relationship between MPO and plaque rupture has not been demonstrated.

The assessment of coronary plaque currently relies on information obtained from the physical contour of the inside of arteries (angiography) and from plaque burden and morphology (optical coherence tomography, intravascular ultrasound). These methods cannot readily detect unstable plaques, many of which are non-obstructive and their rupture is thought to cause up to half of all fatal heart attacks. Therefore, there is an ongoing need for methods for detecting unstable high-risk atherosclerotic plaque to identify and treat subjects at risk of developing acute coronary events. Molecular imaging is attractive in this context, as it images molecules or processes direct involved in atherogenesis and potentially plaque destabilization to non-invasively visualize vulnerable plaque that require special attention.

SUMMARY

The inventors have developed a non-invasive method for detecting unstable atherosclerotic plaque using molecular MRI.

In a first aspect, there is provided a method for detecting unstable atherosclerotic plaque in a subject, for example a human, the method comprising:
a) administering to the subject an MRI contrast agent capable of being activated by myeloperoxidase (MPO) in atherosclerotic plaque;
b) allowing the contrast agent to be activated by MPO in atherosclerotic plaque, resulting in image enhancement;
c) obtaining an image of the atherosclerotic plaque from the subject using molecular MRI,
d) determining from the enhanced imaging one or more of:
ΔCNR,
thickness of a fibrous cap associated with the atherosclerotic plaque; and
fibrous cap:lesion ratio,
wherein a ΔCNR, cap thickness or cap:lesion ratio within a predetermined range indicates that the atherosclerotic plaque is unstable.

In one embodiment the ΔCNR is determined from the enhanced imaging. The predetermined range for ΔCNR is from about 1 to about 80, for example from about 10 to about 30.

In one embodiment the predetermined range for cap thickness is from about 0.01 µm to about 65 µm.

In one embodiment the predetermined range for cap:lesion ratio is from about 10 to about 20.

In one embodiment the predetermined range for ΔCNR is from about 10 to about 30, the predetermined range for cap thickness is from about 0.01 µm to about 65 µm and the predetermined range for cap:lesion ratio is from about 10 to about 20.

The MRI contrast agent may be a gadolinium(III) chelate, for example at least one of bis-5HT-DTPA-Gd (MPO-Gd), mono-5HT-DTPA-Gd, bis-o-dianisidine-DTPA-Gd, mono-o-dianisidine-DTPA-Gd, mono-(5-hydroxytryptophan)-DTPA, (mono-HTrp-DTPA), and bis-(5-hydroxytryptophan)-DTPA, and (bis-HTrp-DTPA).

In an embodiment the gadolinium(III) chelate is bis-5HT-DTPA-Gd.

The method may further comprise:
e) administering to a subject identified as having unstable atherosclerotic plaque, a therapeutically effective amount of a myeloperoxidase inhibitor to stabilise the unstable atherosclerotic plaque.

In one embodiment stabilisation of the unstable atherosclerotic plaque is characterised by at least one of an increase in fibrous cap thickness, an improved ΔCNR, and an increase in the cap:lesion ratio.

For example the increase in fibrous cap thickness may be at least 50%

In an embodiment the MPO inhibitor is selected from the group comprising AZM198, 3-isobutyl-2-thioxo-7H-purin-6-one, 3-[(4-fluorophenyl)methyl]-2-thioxo-7H-purin-6-one, 3-(tetrahydrofuran-2-ylmethyl)-2-thioxo-7H-purin-6-one, 3-[[(2R)-tetrahydrofuran-2-yl]methyl]-2-thioxo-7H-purin-6-one, and 3-(2-methoxyethyl)-2-thioxo-7H-purin-6-one, AZD3241, 2-(6-(5-chloro-2-methoxyphenyl)-4-oxo-2-thioxo-3,4-dihydropyrimidin-1(2H)-yl)acetamide, and PF-1355.

The subject may be a mammalian subject, preferably the subject is a human.

In accordance with the present disclosure, thresholds of MPO activity measured with non-invasive MR imaging may be used to detect enhanced imaging and thus, distinguish unstable from stable plaques. In one or more embodiments, enhanced imaging may be assessed by determining one or more of ΔCNR, thickness (i.e., average thickness and/or minimum thickness) of a fibrous cap associated with the atherosclerotic plaque (for example, using optical coherence tomography (OCT) systems), or the ratio of fibrous cap: lesion, wherein ΔCNR, cap thickness or cap:lesion ratio within predetermined ranges indicates that the atherosclerotic plaque is unstable.

The MRI contrast agent may be a gadolinium(III) chelate. The chelate may comprise a macrocyclic or acyclic ligand functionalised with at least one MPO-activatable moiety. In one or more embodiments, the contrast agent is selected from bis-5-(hydroxytryptamine)-DTPA-Gd (bis-5HT-DTPA-Gd; MPO-Gd), mono-5HT-DTPA-Gd, bis-o-dianisidine-DTPA-Gd, mono-o-dianisidine-DTPA-Gd, mono-(5-hydroxytryptophan)-DTPA (mono-HTrp-DTPA), and bis-(5-hydroxytryptophan)-DTPA (bis-HTrp-DTPA). In alternative embodiments, the contrast agent may comprise a macrocyclic gadolinium(III) chelate, such as 1,4,7,10-tetraazacyclododecane-1,4,7,10-tetraacetic acid (DOTA-Gd), or 10-(2,3-dihydroxy-1-hydroxymethylpropyl)-1,4,7,10-tetraazacyclododecane-1,4,7-triacetic acid (Gadobutrol, GADOVIST®), or the like, wherein the DOTA or Gadobutrol macrocycle is functionalised with one or more MPO-activatable moieties such as 5-HT, o-dianisidine, or 5-HTrp.

In order that the present invention may be more clearly understood, preferred embodiments will be described with reference to the following drawings and examples.

eosinophils. Data show individual values and mean+SD and were analysed by Mann-Whitney rank sum test.

Figure 7:
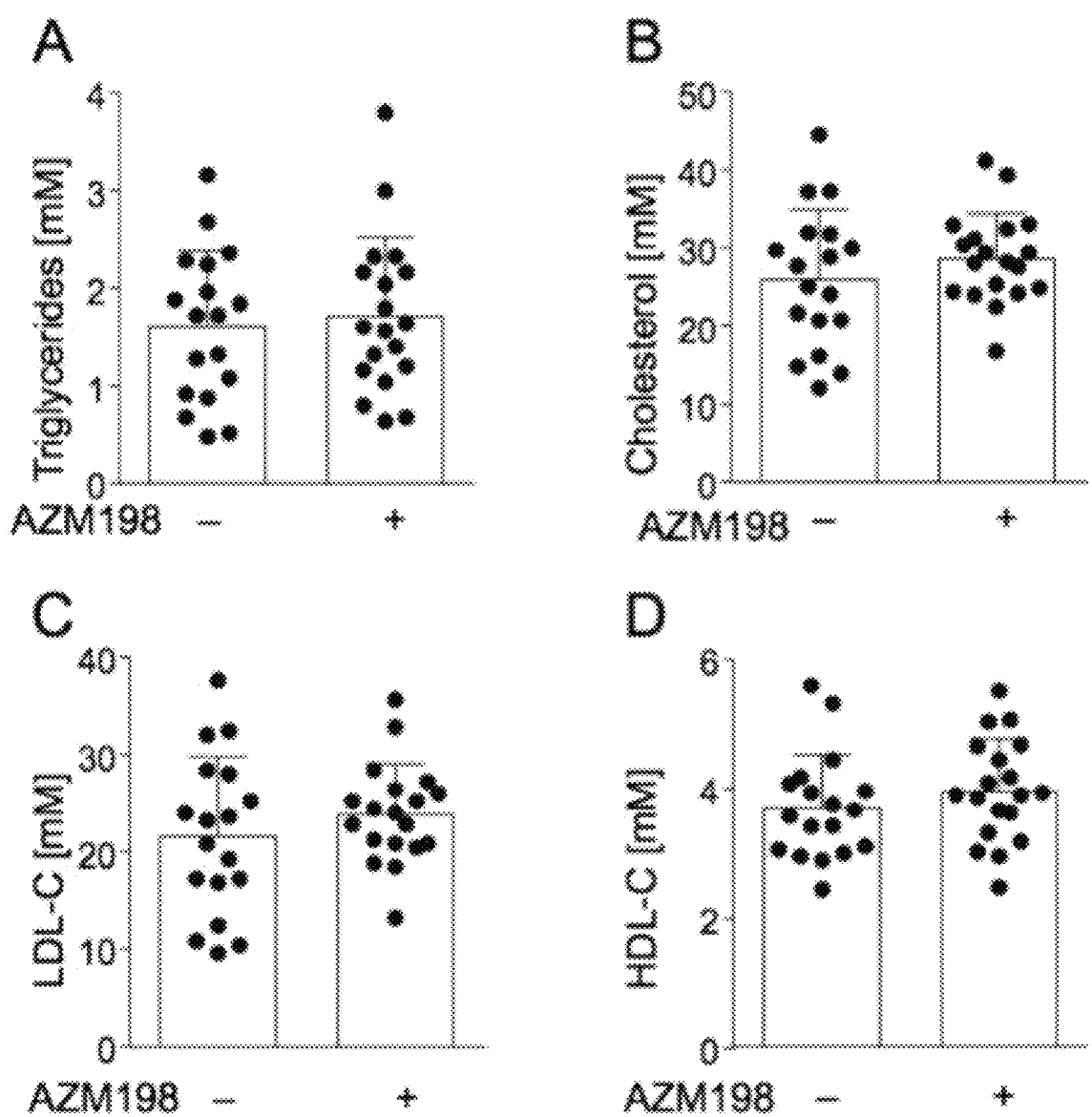

FIG. 7. AZM198 does not affect plasma lipids. At the end of the 13 weeks intervention, heparinised blood was collected from TS mice fed WD without (−) (n=18) or with AZM198 (+) (n=19). Plasma was prepared from blood and analysed for (A) triglycerides, (B) total cholesterol, (C) low density lipoprotein cholesterol (LDL-C) and (D) high-density lipoprotein cholesterol (HDL-C). Data show individual values and mean+SD and were analysed by Mann-Whitney rank sum test.

Figure 8:
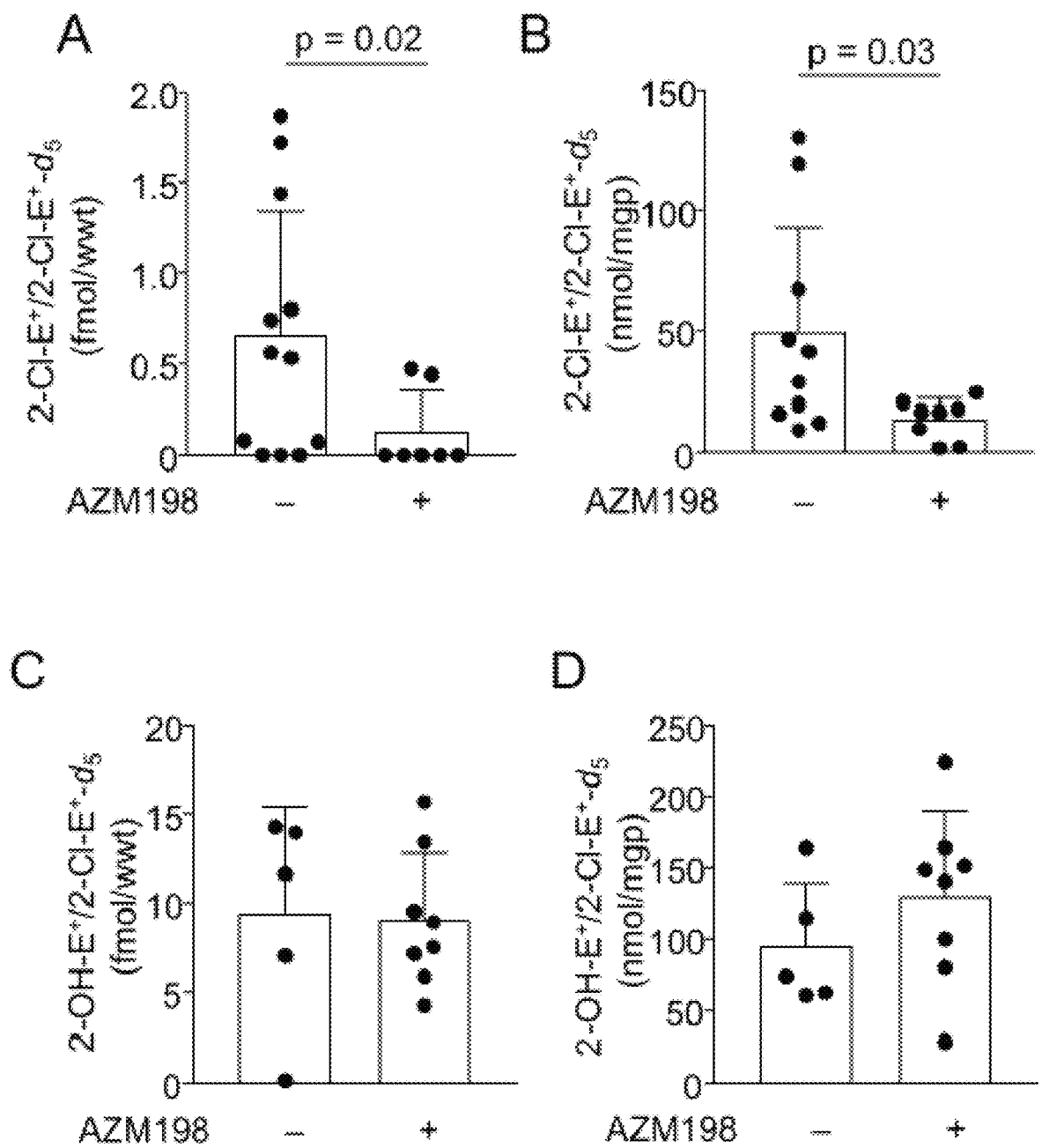
Figure 8:
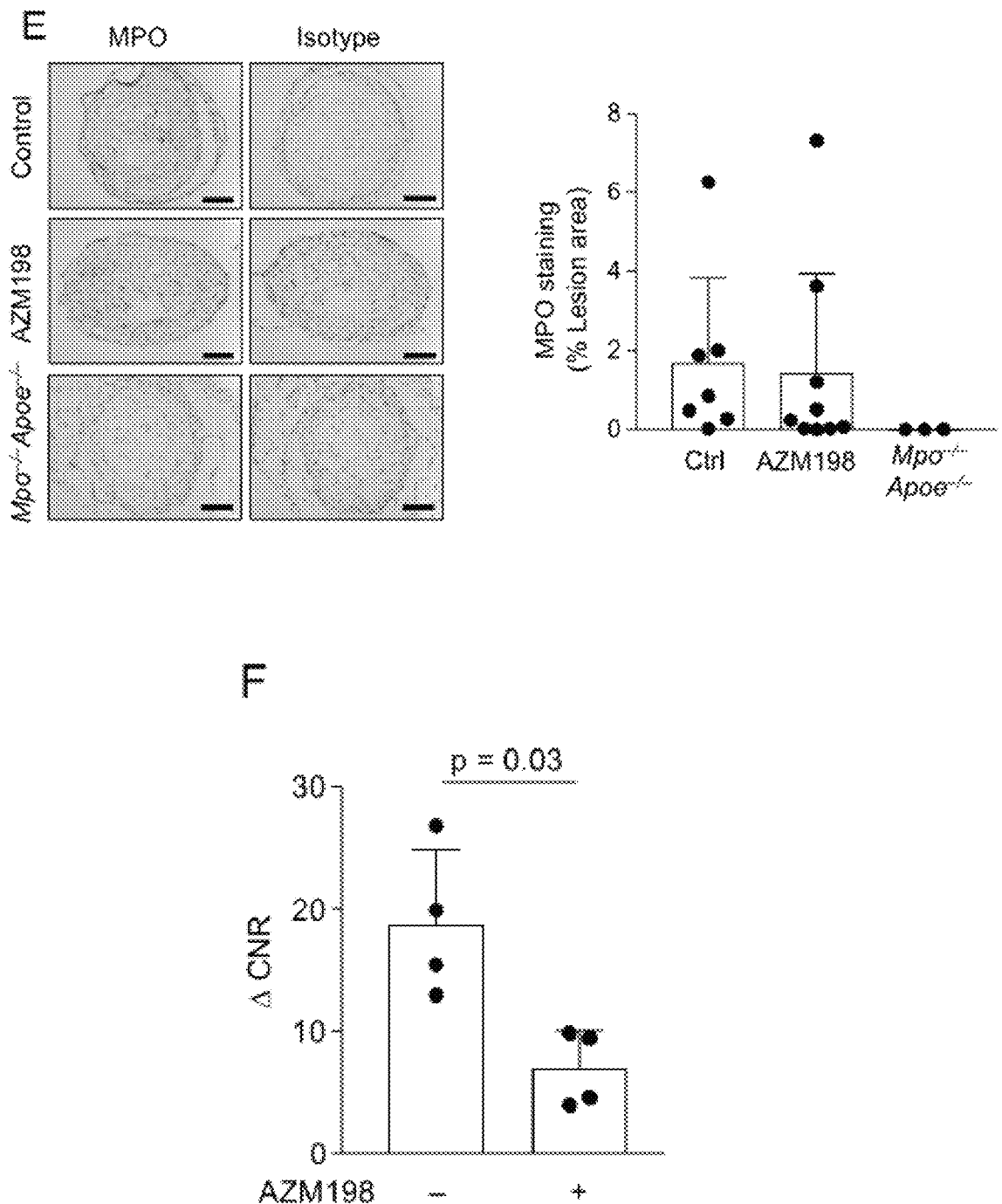

FIG. 8. AZM198 treatment decreases MPO activity in unstable lesions. Unstable plaque from TS Apoe$^{-/-}$ mice fed WD±AZM198 for 13 weeks was analyzed for in vivo (A) and ex vivo 2-chloroethidium (2-Cl-E+) (B) as well as in vivo (C) and ex vivo 2-hydroxyethidium (2-OH-E$^+$) (D) using LC/MS-MS as described in Methods. E, Representative IHC of MPO in unstable plaque from TS mice±AZM198. IHC was performed as described in Methods, using rabbit IgG isotype and sections from Mpo$^{-/-}$Apoe$^{-/-}$ mice as controls, with corresponding quantitative data. Scale bar=100 μm. F, ΔCNR (CNR$_{60\ min}$−CNR$_{precontrast}$) following MPO-Gd T1-TSE. Quantitative data show individual data with mean+SD analysed by Mann-Whitney rank sum test.

Figure 9:
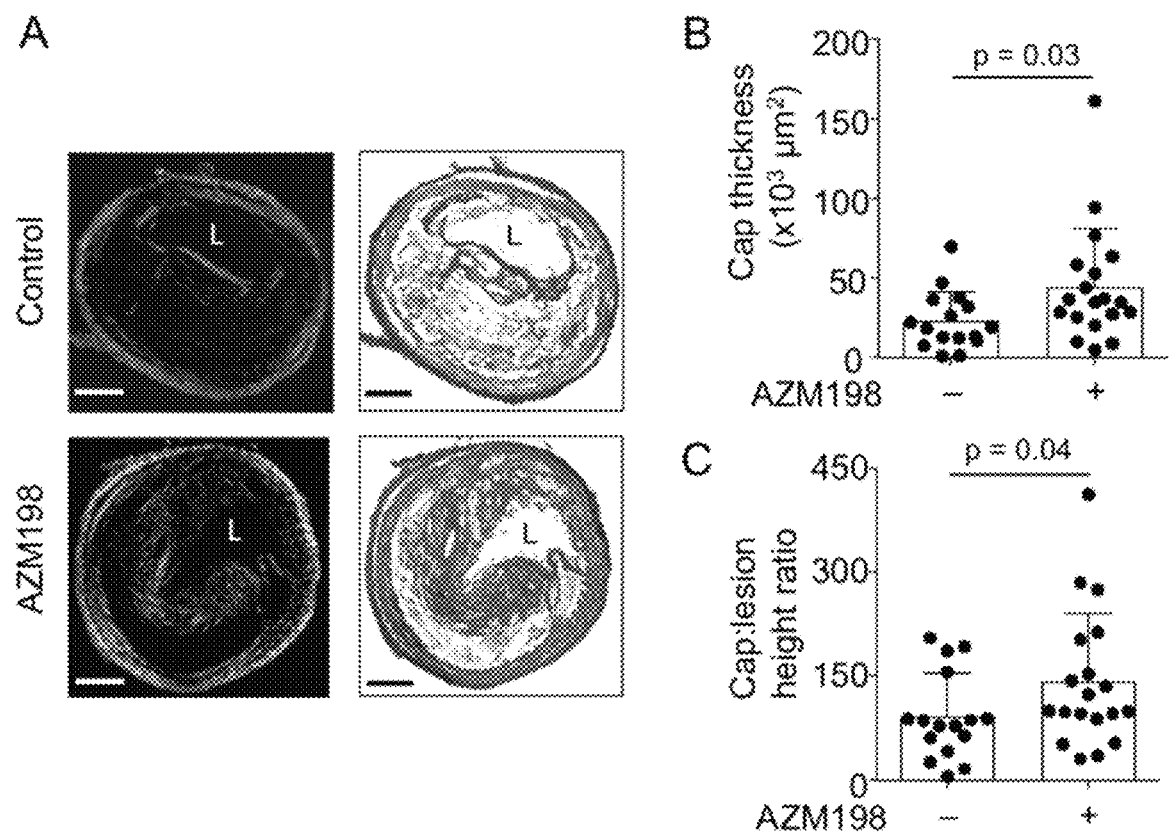

FIG. 9. Pharmacological inhibition of MPO prevents formation of unstable plaque. A, Representative picrosirius red stained sections of unstable plaque viewed under polarised light (left) and bright field (right) in TS Apoe$^{-/-}$ mice fed WD±AZM198 for 13 weeks, with TS surgery performed after 6 weeks of WD±AZM198. Scale bar=100 μm. L, lumen. B, Fibrous cap thickness and (C) cap:lesion height ratio in TS mice fed WD±AZM198. Quantitative data show individual data with mean+SD analysed by Mann-Whitney rank sum test.

Figure 10:
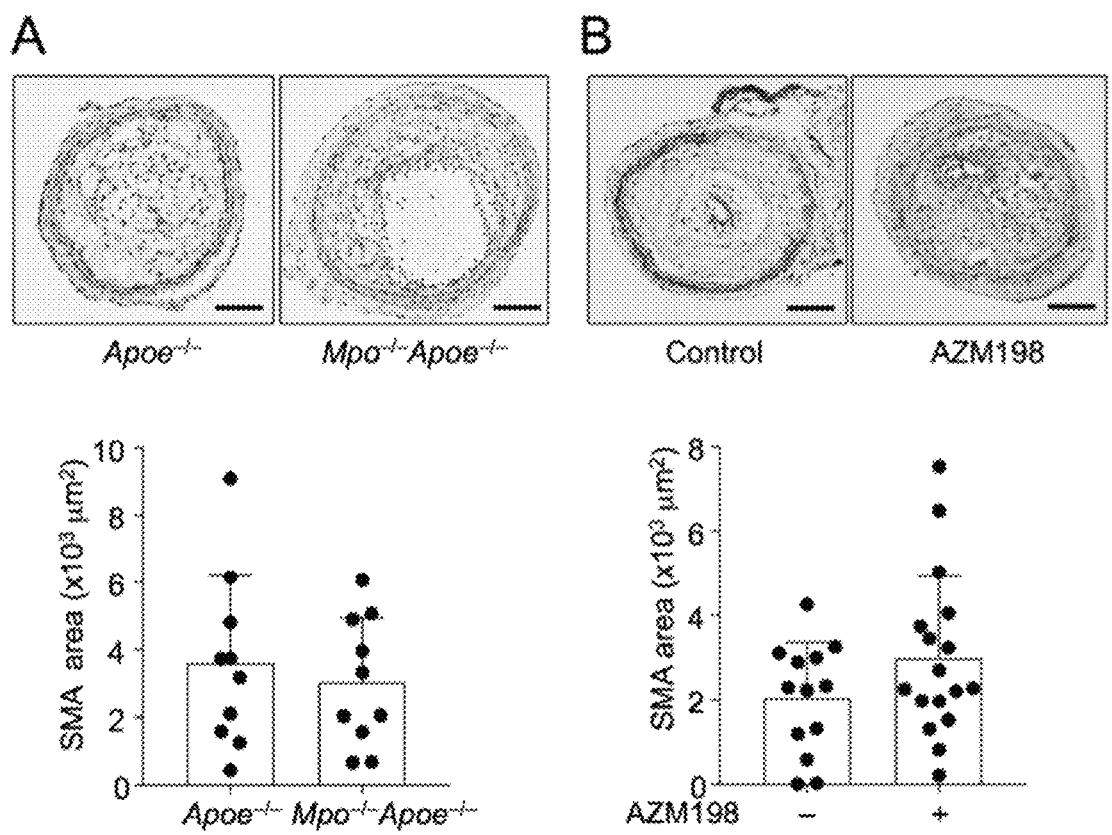

FIG. 10. Effect of AZM198 or MPO deletion on smooth muscle actin content. Unstable plaque was analysed for smooth muscle actin (SMA) content by immunohistochemistry as described in the expanded methods of the supplemental material. A, Representative images of SMA staining in TS Apoe$^{-/-}$ and TS Mpo$^{-/-}$Apoe$^{-/-}$ mice with the corresponding quantitative data showing individual data and mean+SD as SMA+ area. B, Representative images of SMA staining in TS Apoe$^{-/-}$ mice±AZM198 with the corresponding quantitative data showing individual data and mean+SD as SMA+ area. No statistically significant differences were observed (Mann-Whitney rank sum test). Scale bar=100 μm.

Figure 11:
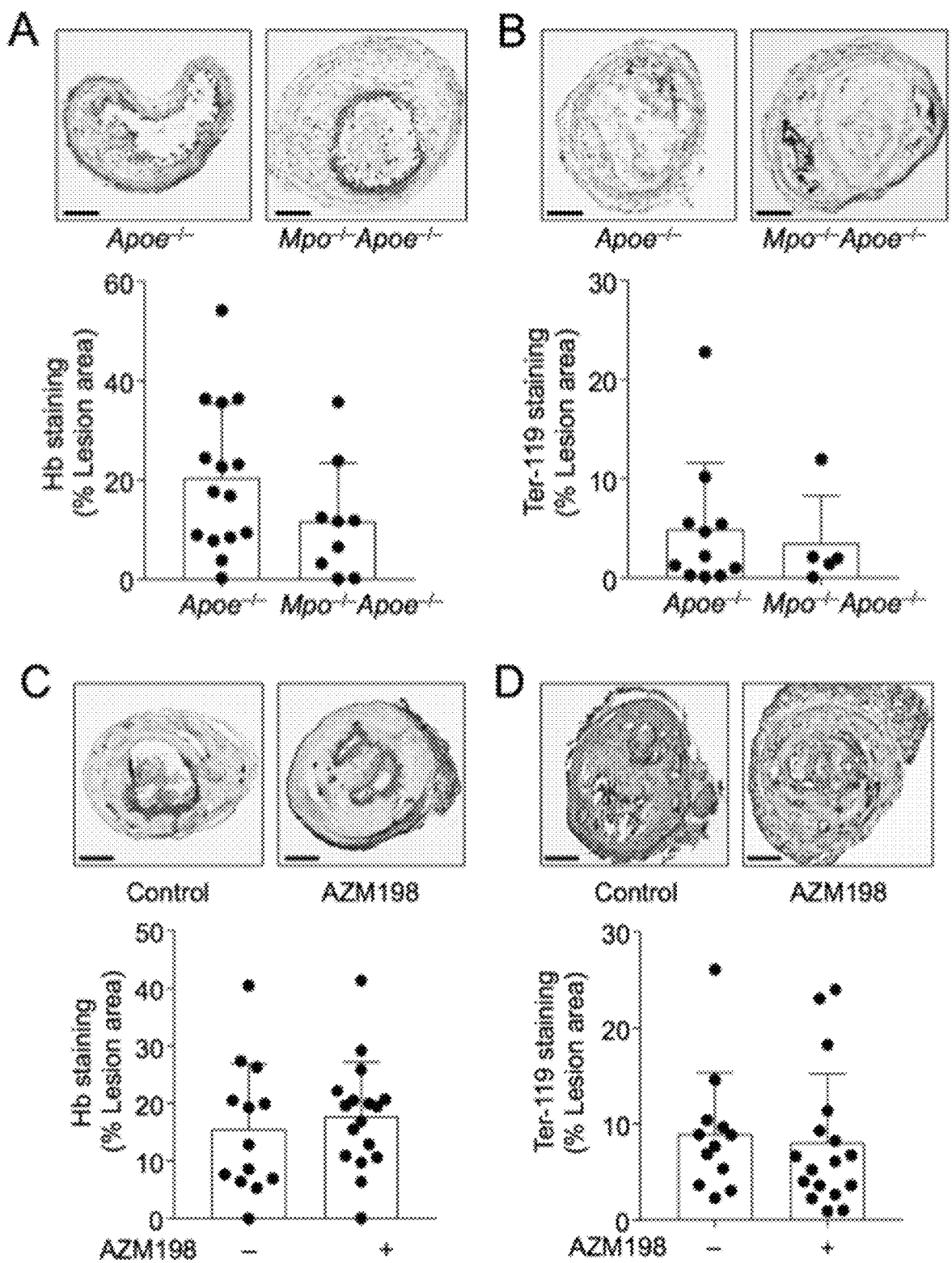

FIG. 11. Effect of AZM198 or MPO deletion on intraplaque haemorrhage. Mice were placed on WD for 13 weeks with TS surgery performed after 6 weeks. Unstable plaque was analysed for the presence of haemoglobin (Hb) and red blood cells. Representative images of Hb for unstable plaque in (A) Apoe$^{-/-}$ and Mpo$^{-/-}$Apoe$^{-/-}$, and TS Apoe$^{-/-}$ mice fed WD±AZM198 (C) and corresponding quantitative data showing individual data and mean+SD as Hb+ area calculated as percentage of stained areas per total lesion area. Representative images of Ter-119 staining, a mouse red blood cell marker, for unstable plaque in (B) Apoe$^{-/-}$ and Mpo$^{-/-}$Apoe$^{-/-}$, and TS Apoe$^{-/-}$ mice fed WD±AZM198 (D) and corresponding quantitative data showing individual data and mean+SD as stained area per total lesion area. Numeric data shows mean+SD. No statistically significant differences were observed (Mann-Whitney rank sum test). Scale bar=100 μm.

Figure 12:
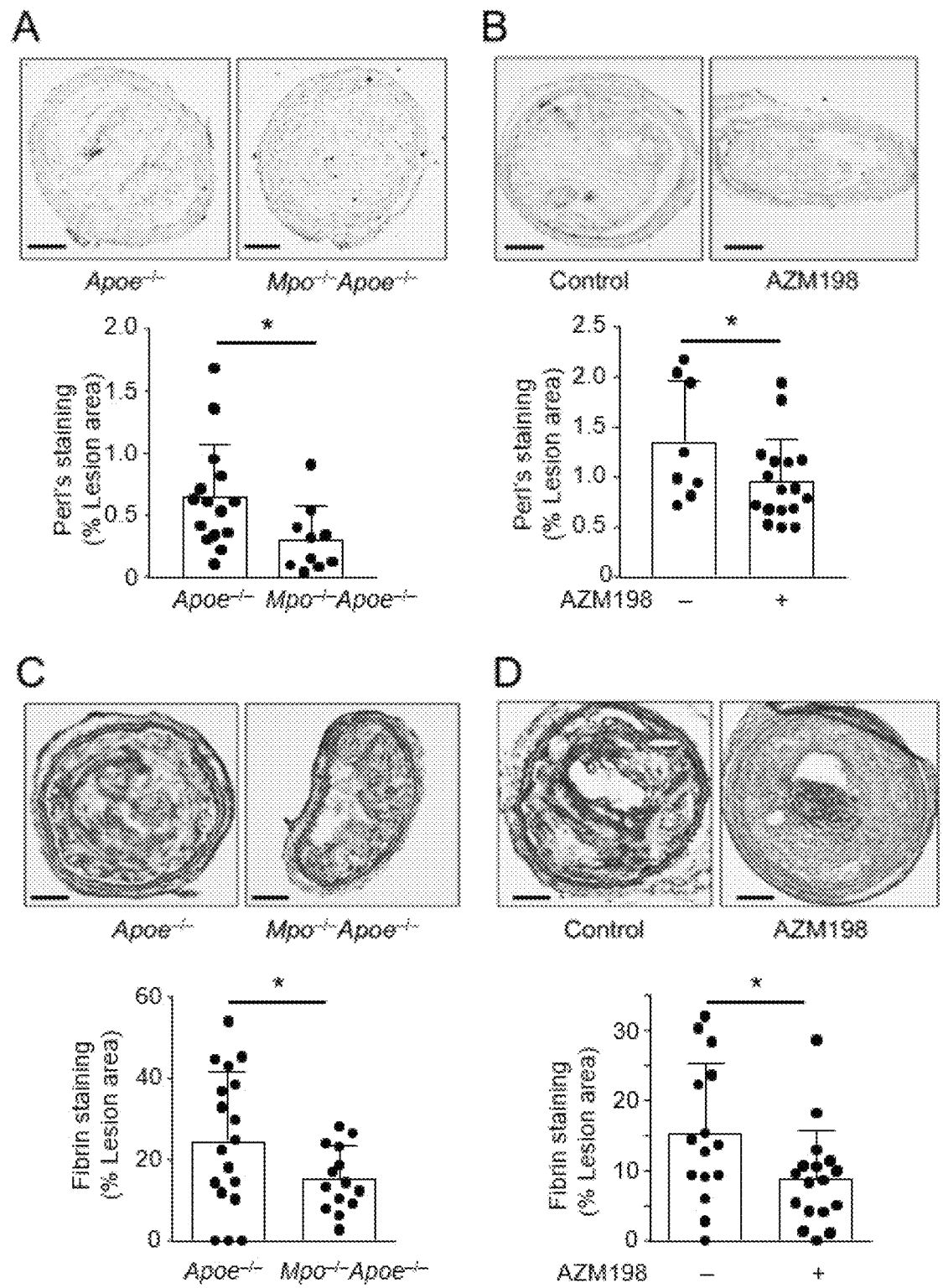

FIG. 12. Effect of AZM198 on intraplaque fibrin and haemosiderin. Unstable plaque was assessed by Perl's Prussian Blue and Martius Scarlet Blue (MSB) staining in TS Mpo$^{-/-}$Apoe$^{-/-}$ and TS Apoe$^{-/-}$ mice±AZM198 to detect haemosiderin and fibrin, respectively. A and B, Representative images of Perl's staining and quantification of haemosiderin+ area expressed as percentage per total lesion area. C and D, Representative images of lesion fibrin (bright red stain) by MSB staining with quantification showing percentage fibrin+ area per total lesion area. Quantitative data show individual data with mean+SD analysed by Mann-Whitney rank sum test (A, B, D) and unpaired t-test (C). Scale bar=100 μm.

Figure 13:
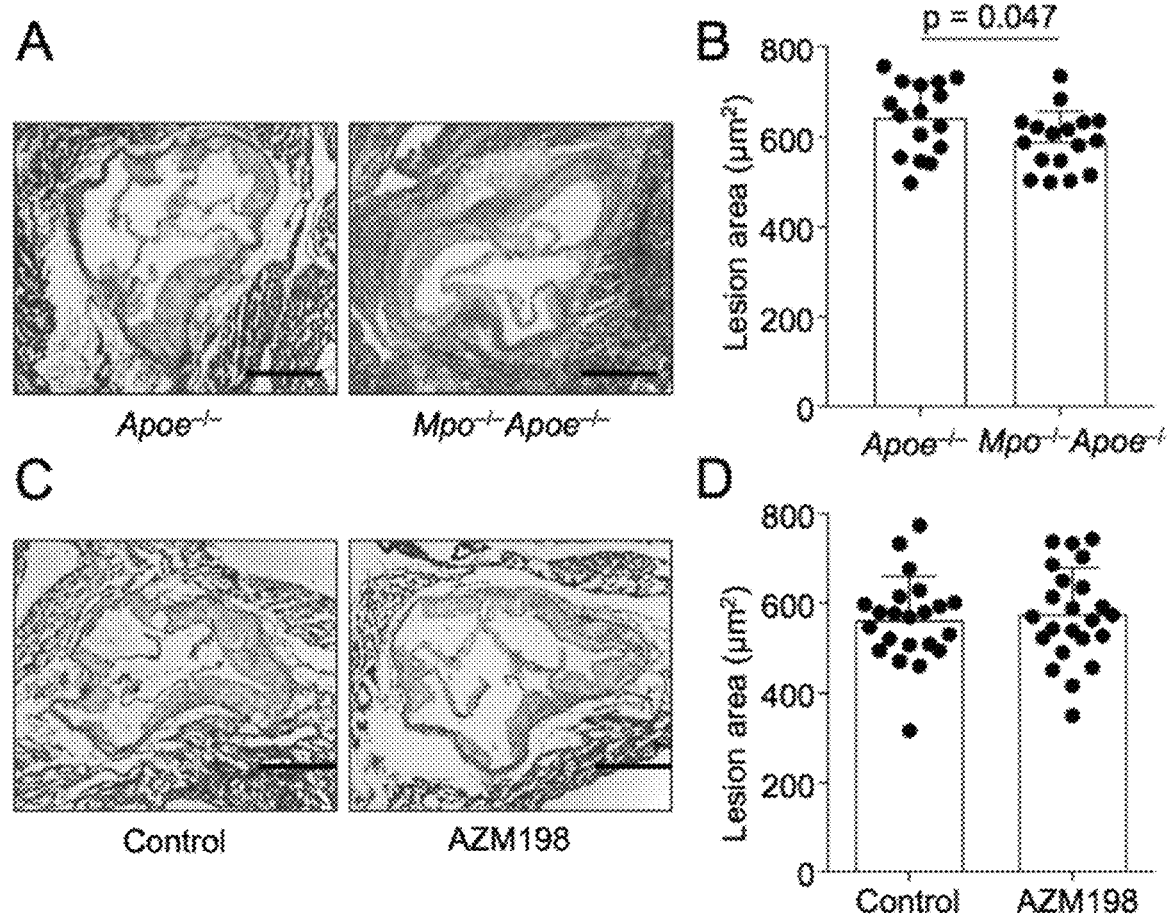

FIG. 13. Effect of MPO deletion or AZM198 on the size of atherosclerotic lesions. TS mice were fed Western Diet±AZM198 for 13 weeks with TS surgery after six weeks. Following the intervention, the size of atherosclerotic lesions in the aortic root was assessed by morphometry as described previously (Arterioscler Thromb Vasc Biol. 2000; 20:e26e33). A and B, Representative H&E stained sections of the aortic root from Apoe$^{-/-}$ (n=16) versus Mpo$^{-/-}$Apoe$^{-/-}$ (n=17) and quantification of atherosclerotic lesion size. C and D, Representative H&E stained sections of the aortic root from TS mice without (−) (n=25) and with (+) AZM198 treatment (n=25) and quantification of lesion size. Numeric data show individual values with mean+SD, analysed by the Mann-Whitney rank sum test. Scale bar=250 μm.

Figure 14:
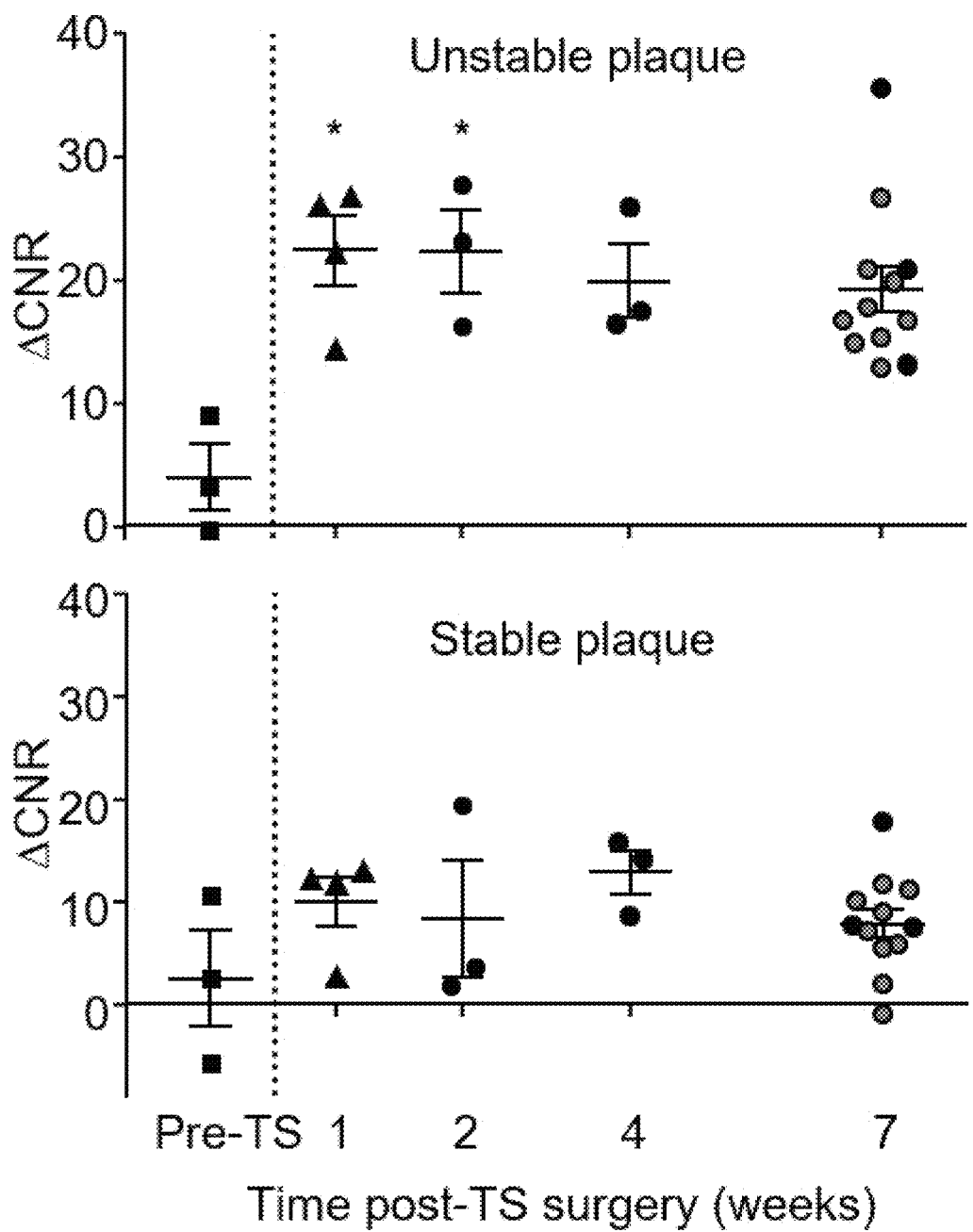
Figure 14:
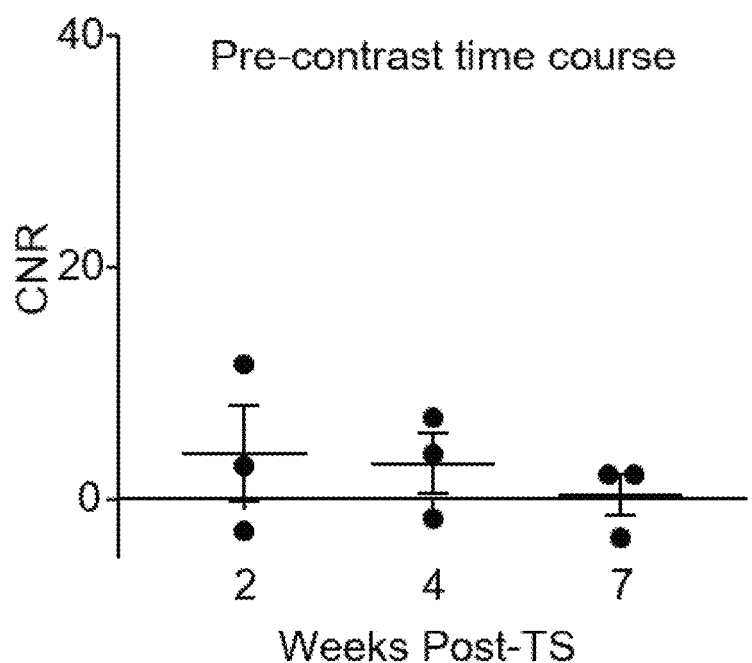
Figure 14:
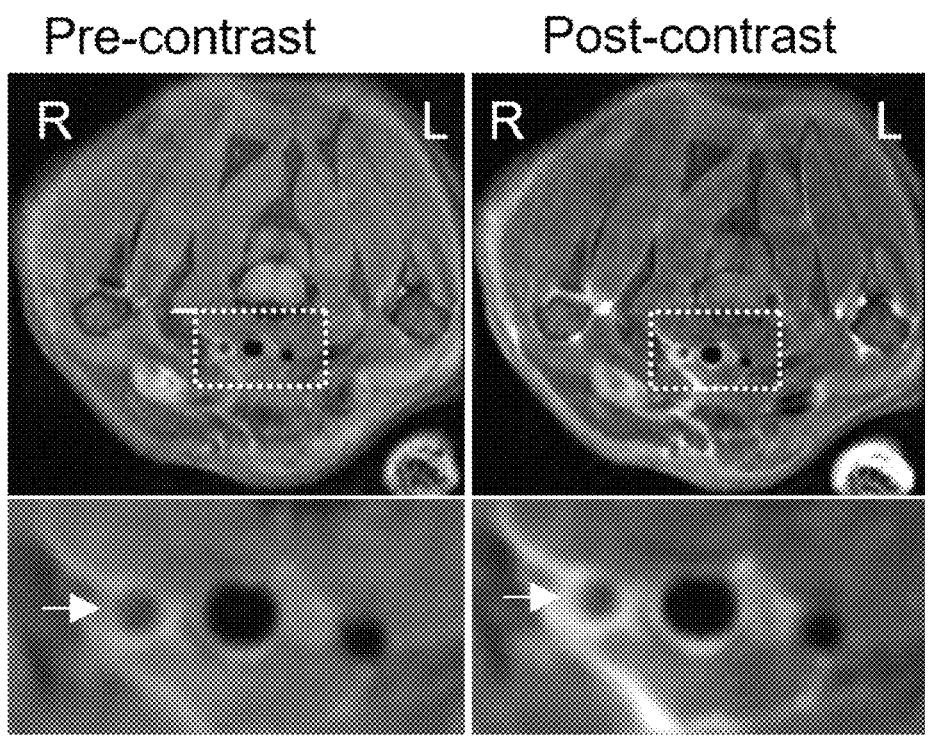
Figure 14:
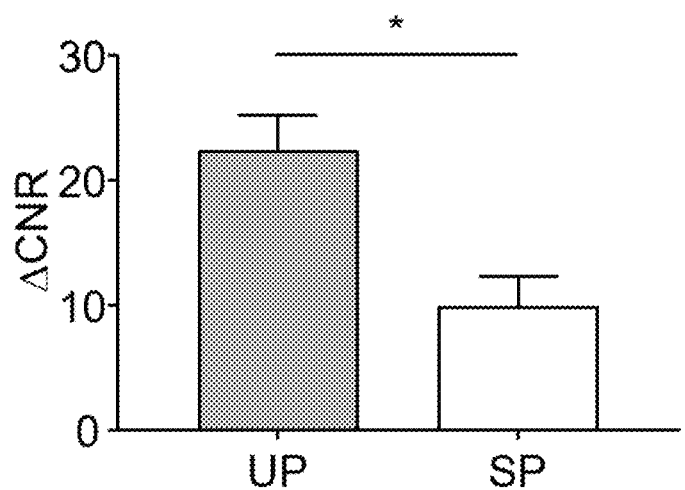
Figure 14:
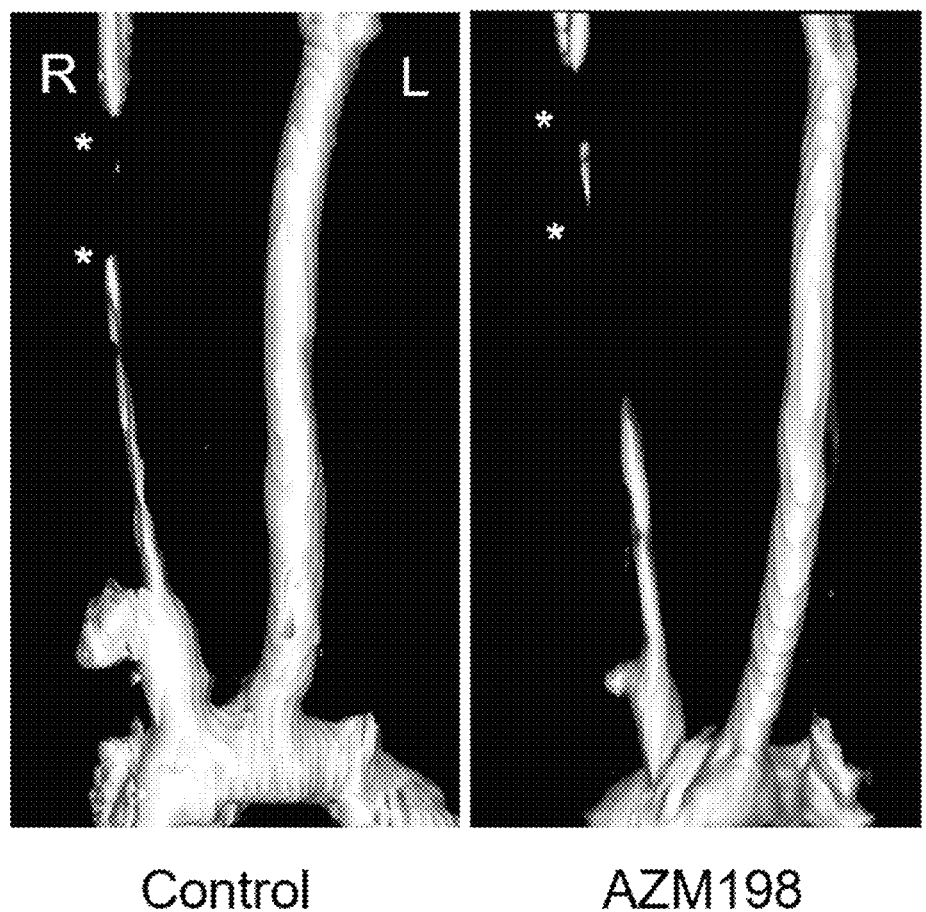
Figure 14:
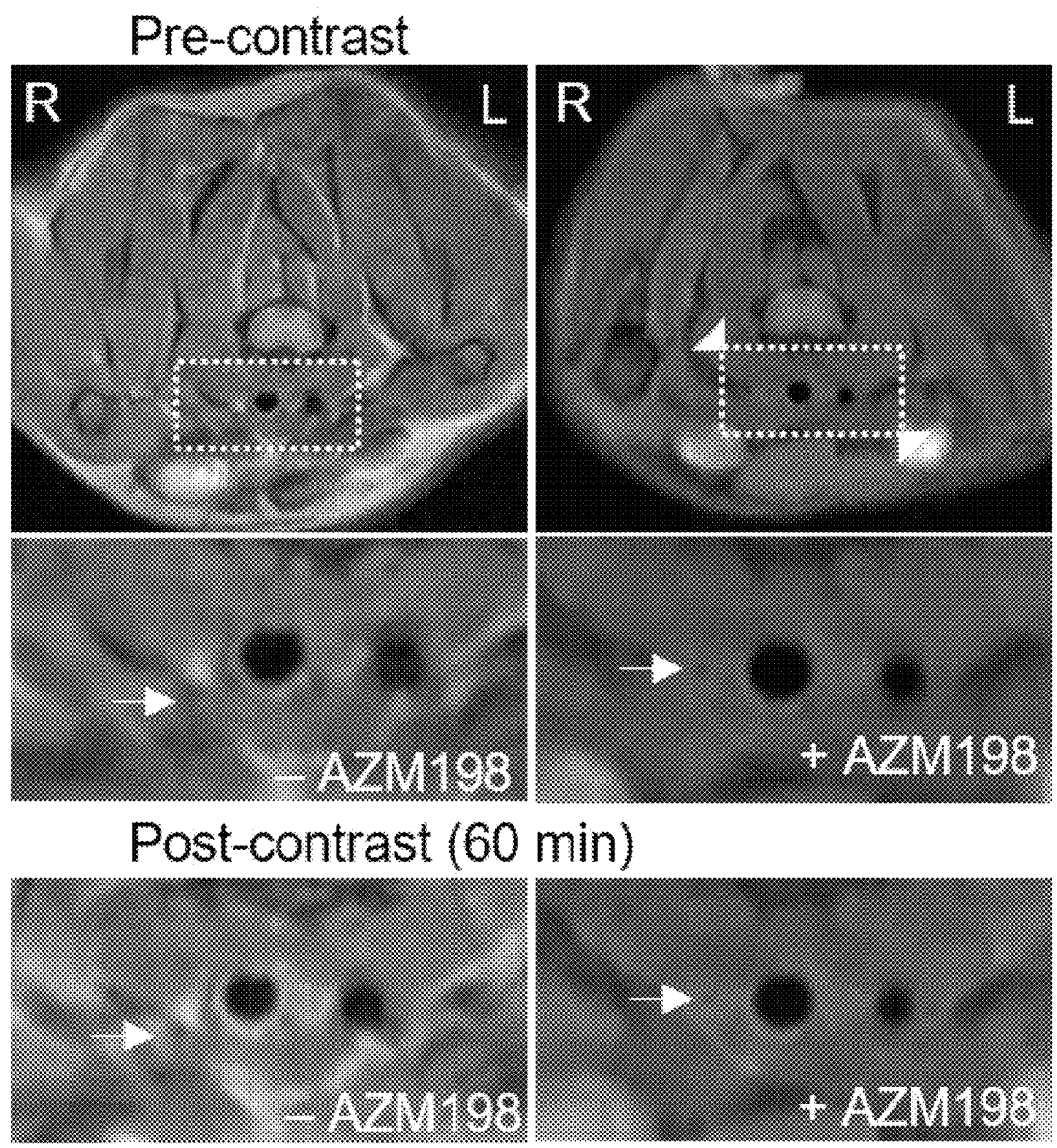
Figure 14:
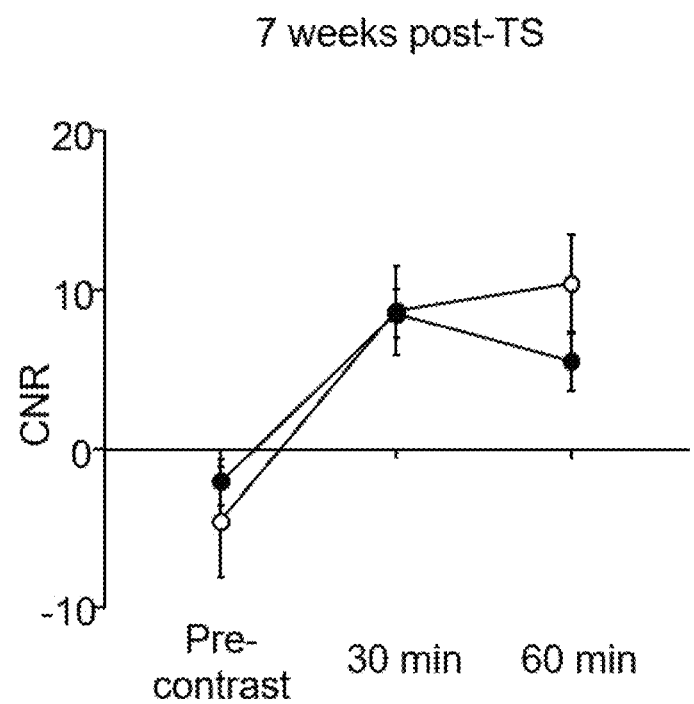
Figure 14:
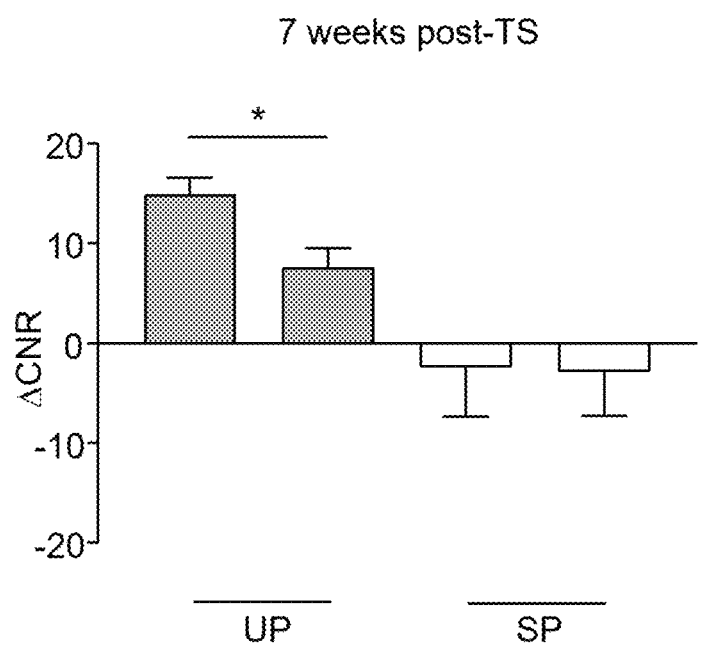

FIG. 14. Pharmacological inhibition of MPO stabilizes unstable plaque as assessed by molecular MRI using contrast agent activated by MPO. A: Time-dependent increase in ΔCNR before and after TS surgery of Apoe$^{-/-}$ mice indicating formation of unstable plaque as early as 1 week after TS surgery. B: Pre-contrast ΔCNR values for the 3 μmice undergoing repeated MRI after TS surgery. C: Representative T1 images at 1 week post-TS surgery. D: MRI enhancement 1 week post-TS surgery is significantly increased in unstable plaque (UP, referred to as "" in Circ Res. 2013; 113:252-265) compared with stable plaque (SP, brachiocephalic artery). E: Representative time-of-flight angiography of the right (R) and left (L) carotid artery from a control and an AZM198 treated mouse 7 weeks post-TS, with treatment with AMZ198 beginning 1 week post-TS, i.e., a time when ΔCNR had reached maximal value as shown in (A). Asterisks indicate the sites where ligatures were placed. F: Representative pre-contrast and post-contrast (60 μmin) images, showing enhancement in the right carotid artery ("Segment I"). G: CNR time course of control (open circle) and AZM198 treated (starting 1 week after TS surgery) mice. H: Comparison of ΔCNR for unstable (UP) and stable plaques (SP) of both control and AZM198-treated (starting 1 week after TS surgery) mice.

DEFINITIONS

Throughout this specification, unless the context requires otherwise, the word 'comprise', or variations such as 'comprises' or 'comprising', will be understood to imply the inclusion of a stated element, integer or step, or group of elements, integers or steps, but not the exclusion of any other element, integer or step, or group of elements, integers or steps.

Throughout this specification the term 'consisting of' refers to compositions, methods, and respective components thereof as described herein, which are exclusive of any element not recited in that description of the embodiment. That is, the term 'consisting of' means 'consisting only of'.

As used herein, the term 'subject' refers to an individual who will receive or who has received treatment (e.g., administration of a compound described herein) according to a method described herein, or who has a disease or disorder or undesired physiological condition associated with atherosclerotic plaque. A subject may also be an individual in whom the formation of atherosclerotic plaque is to be prevented. In preferred embodiments the subject is a mammalian subject, preferably a human.

As used herein the term 'therapeutically effective amount' refers to an amount of a therapeutic agent, such as an MPO inhibitor, or combination of MPO inhibitors, sufficient to stabilise, prevent or inhibit the formation of unstable plaque in an organ or tissue of a subject. In some embodiments the amount is sufficient to reduce the number of observable unstable plaques.

As used herein, the term 'treatment' refers to a clinical intervention made in response to a disease, disorder or physiological condition manifested by a subject or to which a subject may be susceptible. The aim of treatment includes, but is not limited to, the alleviation or prevention of symptoms, slowing or stopping the progression or worsening of unstable plaque, and/or the reducing the amount of unstable plaque. 'Treatment' refers to one or both of therapeutic treatment and prophylactic or preventative measures. In accordance with the present disclosure, subjects in need of treatment include those already affected by unstable plaque, as well as those in whom formation of unstable plaque is to be prevented or at least reduced.

As used in this specification and the appended claims, the singular forms 'a,' 'an,' and 'the' include plural references unless the context clearly dictates otherwise. Thus for example, references to 'the method' include one or more methods as described herein and/or which will become apparent to those persons skilled in the art upon reading this disclosure.

Throughout this specification the terms 'MRI contrast agent', 'contrast agent' are used interchangeably and, unless the context clearly dictates otherwise, refer to an agent that increases the contrast between different parts of a sample or tissue by altering the relaxation times of hydrogen nuclei of water during MRI.

Throughout this specification, the terms 'functionalised MRI agent', 'functionalised agent', 'MPO-activatable MRI contrast agent' and 'MPO-activatable contrast agent' are synonymous and used interchangeably and refer to an MRI contrast agent that is functionalised with at least one moiety that is a substrate for the MPO enzyme and capable of being oxidised (or 'activated') by MPO.

Any discussion of documents, acts, materials, devices, articles or the like which has been included in the present specification is solely for the purpose of providing a context for the present invention. It is not to be taken as an admission that any or all of these matters form part of the prior art base or were common general knowledge in the field relevant to the present invention as it existed before the priority date of each claim of this specification.

DESCRIPTION

The inflammatory enzyme, MPO, is abundant in ruptured human atherosclerotic plaques. The technology disclosed herein relates to non-invasive Magnetic Resonance Imaging (MRI) based methods for identifying and clinically assessing the location and size of unstable atherosclerotic plaques in the vasculature of a subject. More particularly, the methods may be used to differentiate stable and unstable plaques by evaluating the prevalence of MPO in atherosclerotic plaque, wherein a high proportion of MPO manifests as enhanced imaging which is indicative of high risk (unstable) plaque.

MRI is a well-known technique that non-invasively produces a three dimensional image by placing a subject in a magnetic field and exciting the nuclear spins of water protons using radio frequency pulses. The radio frequency pulse shifts the proton spins out of alignment with the magnetic field. As the spins relax back to alignment, energy is released which can be measured and used to produce an image. The signal intensity in a given volume is proportional to the concentration of water protons and the rates that they relax. There are two major relaxation rates: 'longitudinal' relaxation for T1, and 'transverse' relaxation for T2.

MRI methodologies using gadolinium contrast agents are known in the art and are within the knowledge of the skilled person.

MRI Contrast Agents

The methods disclosed herein involve administration of a functionalised MRI contrast agent to a subject. More specifically, the functionalised contrast agent is delivered to a cell, tissue or organ of interest, for example the vasculature. In one or more embodiments, a functionalised contrast agent is administered to an atherosclerotic plaque. In various embodiments, delivery is systemic and the functionalised contrast agent is taken up into plaque.

In other embodiments the functionalised contrast agent may be taken up by cells, tissues or organs that do not contain plaque, but preferably this does not have a significant negative effect on such cells or tissues, or on the subject as a whole. In such embodiments, the uptake of functionalised contrast agent by cells, tissues or organs that do not contain plaque may be a marker of inflammation, including vascular inflammation, such as that associated with rejection of a transplanted organ (e.g., heart), a heart damaged after myocardial infarction or heart failure, and the like. Accordingly, in some embodiments the methods disclosed herein may be useful for detecting inflammation in a tissue or organ of a subject.

Methods for administration of contrast agents are well known in the art and are applicable to the administration of functionalised contrast agents as disclosed herein. Thus, in one embodiment the functionalised contrast agent may be administered by injection, for example intravenous or intra-arterial injection. In some embodiments the functionalised contrast agent may be administered to a subject via a catheter, for example when the subject is undergoing a combined MRI and radiographic catheter procedure.

The functionalised contrast agent may be administered by, or under the supervision of a physician who will determine the concentration, volume, and route of administration of the contrast agent.

The Gd(III) ion is a paramagnetic rare earth metal commonly used in MRI contrast agents to enhance clinical MR images. Gd(III) advantageously has a property referred to as relaxivity, which improves contrast by reducing the T1 relaxation rate of nearby protons from water. Gd(III) creates an area of increased brightness in an MRI image because the intensity of the MRI signal is proportional to the relaxation rate of water. The increased signal intensity can be used to improve resolution, reduce acquisition times, and/or investigate a location of interest.

Gadolinium chelates based on the macrocyclic 1,4,7,10-tetraazacyclododecane-1,4,7,10-tetraacetic acid (DOTA) ligand or the acyclic diethylenetriaminepentaacetic acid (DTPA) ligand are clinically approved imaging agents for use in cardiovascular MRI. Macrocyclic contrast agents may present a lower risk of gadolinium toxicity resulting from gadolinium release and uptake, relative to acyclic ligands. This may be advantageous in a clinical setting for example, in multiple or longitudinal MRI studies, such as studies for targeting efficacy of a novel drug or unstable plaque.

As described by Rodriguez E. et al. *J Am Chem Soc* 2010; 132:168-177, the MPO catalytic center consists of a heme group that can undergo redox reaction. In the presence of $H_2O_2$, the native enzyme can be oxidized to form a redox intermediate compound, which can transform halides, particularly Cl—, into hypochlorous acid (HOCl). This redox intermediate compound is also capable of catalysing the oxidation of functionalised aromatic substrates, such as tyrosine or 5-hydroxytryptamine (5HT), through $1e^-$ oxidation.

Representative examples of redox-active MPO substrates include 5-hydroxytryptamine (5-HT), 5-hydroxytryptophan (5-HTrp), O-dianisidine, guaicol, urate, estradiol, tyrosine, norepinephrine, ascorbate, phenols, aniline, halides, thiocyanate and nitrite, among others.

In accordance with the present technology, the functionalised contrast agent has redox properties that enable it to be activated by MPO. As disclosed herein, the contrast agent may be derived from DOTA, DTPA or other suitable chelate capable of binding gadolinium, functionalised with at least one suitable redox active group that is a substrate for MPO. In preferred embodiments disclosed herein, the contrast agent is a functionalised DTPA gadolinium chelate having at least one redox active group (MPO substrate moiety).

Functionalised contrast agents that are suitable substrates for MPO may be identified on the basis of their reduction potential. In preferred embodiments, reduction potential of the substrate is lower than 0.97 V. The contrast agent may comprise one or more redox active MPO substrates. Preferably, the contrast agent comprises one or two redox active MPO substrates. For example, the contrast agent may comprise one or more 5-hydroxytryptamine (5-HT), 5-hydroxytryptophan (5-HTrp), O-dianisidine moieties.

Representative examples of functionalised contrast agents include bis-5HT-DTPA-Gd (MPO-Gd), mono-5HT-DTPA-Gd, bis-o-dianisidine-DTPA-Gd, mono-o-dianisidine-DTPA-Gd, mono-(5-hydroxytryptophan)-DTPA (bis-HTrp-DTPA), and bis-(5-hydroxytryptophan)-DTPA, (bis-HTrp-DTPA). In alternative embodiments, the contrast agent may comprise a macrocyclic gadolinium(III) chelate, such as 1,4,7,10-tetraazacyclododecane-1,4,7,10-tetraacetic acid (DOTA-Gd), or 10-(2,3-dihydroxy-1-hydroxymethylpropyl)-1,4,7,10-tetraazacyclododecane-1,4,7-triacetic acid (Gadobutrol, GADOVIST®), or the like, wherein the DOTA or Gadobutrol macrocycle is functionalised with one or more MPO-activatable moieties such as 5-HT, o-dianisidine, or 5-HTrp. In preferred embodiments the contrast agent is bis-5-hydroxytryptamine-DTPA Gd (MPO-Gd).

These and other functionalised contrast agents may be prepared using methods known in the art, including, for example, the methods described by Rodriguez E. et al. *J Am Chem Soc* 2010; 132:168-177; Shazeeb et al., Mol Imaging. 2012 September-October; 11(5): 433-443.

Figure 2:
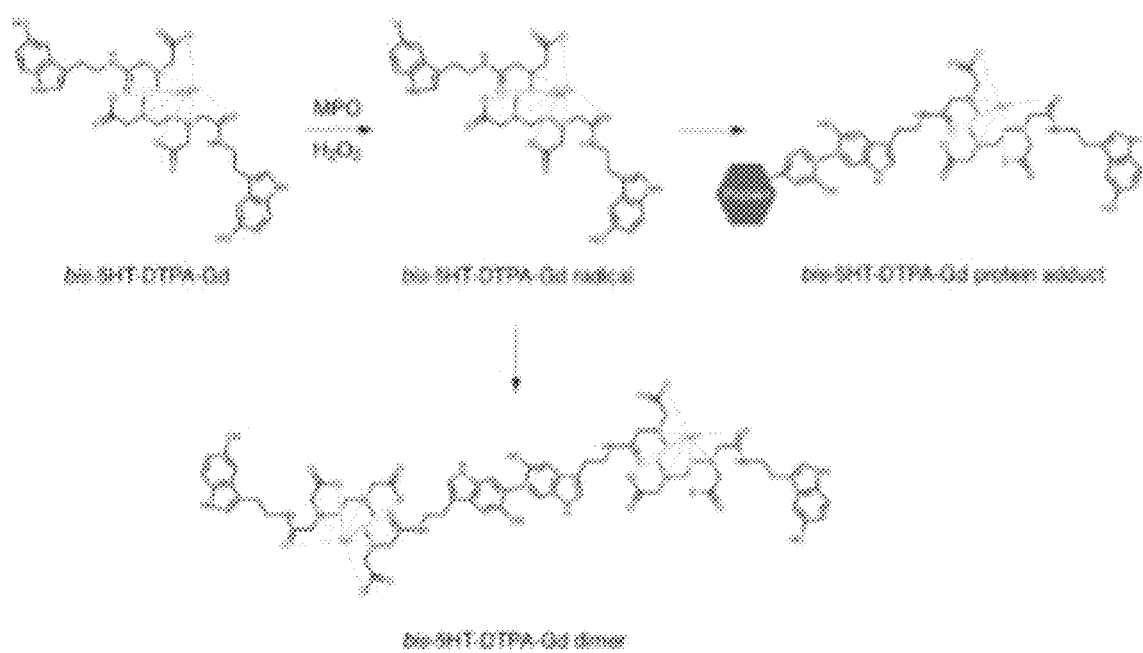
FIG. 2. Scheme of action of bis-5HT-DTPA-Gd (MPO-Gd) and magnetic resonance imaging protocol. A, In the presence of $H_2O_2$, MPO oxidises the 5-hydroxytryptamine moiety of MPO-Gd to a phenoxyl radical, which then can give rise to either an MPO-Gd dimer or multimer (not shown) to amplify the signal. The phenoxyl radical-containing MPO-Gd may also covalently bind to proteins. This results in the retention of MPO-Gd in target tissues. B, Mice were imaged under isoflurane anaesthesia. Initial acquisition involved a localiser, time-of-flight and T1-weighted turbo spin echo (T1-TSE) imaging. Approximately 30 μmin after acquisition of baseline images, MPO-Gd (0.3 mmol/kg) was injected intravenously via the tail vein. Consecutive T1-TSE images were then acquired for 60 μmin following contrast injection. Segmental analysis of MPO activity was assessed by calculating the ΔCNR ($CNR_{post-contrast}$–$CNR_{pre-contrast}$) for unstable and stable plaque, and non-diseased arterial segments.
Figure 2:
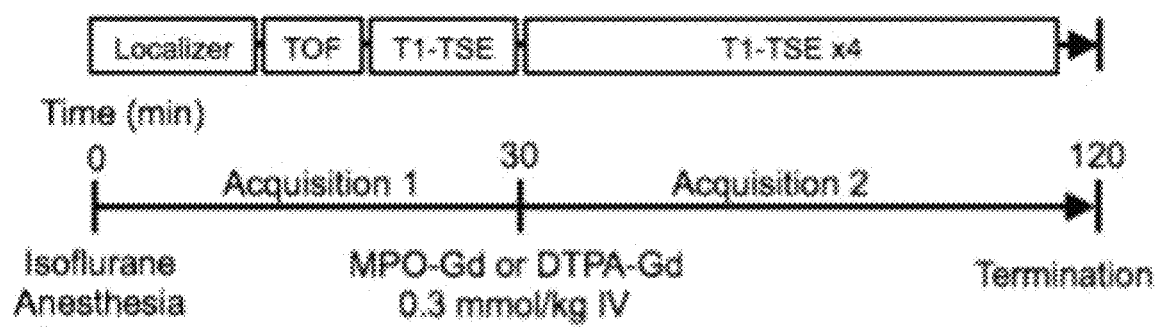

By way of illustration, FIG. 2 shows that in the presence of $H_2O_2$, MPO oxidises the 5-hydroxytryptamine moiety of MPO-Gd to a phenoxyl radical, which then can give rise to an MPO-Gd dimer or oligomer (not shown) to amplify the signal. Alternatively, or in addition, the phenoxyl radical-containing MPO-Gd may covalently bind to endogenous proteins, which results in the retention of MPO-Gd in target tissues.

The functionalised contrast agent may provide enhanced spin-lattice-relaxivity, that is, increased molar relaxivity (r1 and r2) of the paramagnetic contrast agents. In addition, as the products of the redox reaction may be retained in the tissue for longer periods of time than the original substrates, direct MR imaging of MPO activity in vivo is possible.

The detection and diagnostic methods require activation of the contrast agent by MPO in an atherosclerotic plaque. After administration of the contrast agent, particularly systemic administration a period of time is required to allow the contrast agent to reach the atherosclerotic plaque and become activated by MPO in the plaque. For example this period of time may be 5, 10, 15, 20, 25, 30, 40, 45, 50 or 60 µminutes, or longer.

Diagnostic Step: Imaging

Any conventional MR imaging technique may be used in the methods disclosed herein. For example, in some embodiments, inversion recovery sequences (for example IR-FLASH or IR-SSFP) may be used.

Exemplified embodiments disclosed herein utilise T1-weighted imaging (e.g., T1-weighted turbo spin echo (T1-TSE) imaging) to determine the prevalence of MPO in atherosclerotic plaque, wherein enhanced imaging is indicative of unstable plaque. In one embodiment a T1-weighted approach is used in which most of the contrast between tissues or tissue states is due to differences in tissue T1. A T1 contrast state is approached by imaging with a short TR (repetition time) compared to the longest tissue T1 of interest and short TE (echo time) compared to tissue T2 (to reduce T2 contributions to image contrast). Due to the wide range of T1 and T2 and tissue density values that can be found in the body the TE and TR will be different for different tissues but within knowledge of the skilled person.

In some embodiments a number of spin echoes are combined into a single image of image set in multiple echo imaging sequences. This is applicable to techniques such as rapid acquisition with relaxation enhancement (RARE), fast-spin echo (FSE), and turbo spin-echo (TSE). The number of echoes combined into a single image or image set is known as the echo train length (ETL). One echo train technique that may be used is rapid acquisition with relaxation enhancement (RARE) in which the ETL typically equals the acceleration factor.

The parameters for any MRI method used will be determined by the nature of the contrast agent used, the location of the plaques being imaged and the nature of the subject (e.g. size, weight, age, general health etc). Such parameters can be determined by conventional techniques known to the skilled person.

The contrast agents described herein allow the use of MRI to assess MPO activity in plaque. Accordingly, MR images can be used to assess the location and size of unstable atherosclerotic plaques in the vasculature.

Unstable atherosclerotic plaque is characterized by a 'soft' atheromatous core (which may become necrotic) overlaid by a fibrous cap. Unstable plaque is prone to rupture following which highly thrombogenic components are exposed to flowing blood. This leads to thrombus formation at the plaque and consequential infarction of tissue distal to the thrombus, either because of thrombus formation at the plaque or because thrombus fragments break off and block smaller vessels distal to the plaque.

As disclosed herein, increased MPO activity is indicative of unstable plaque and imaging MPO activity can be used to assess cap thickness and to assess the cap to lesion ratio, i.e., the ratio of the cap thickness to the thickness of the entire plaque.

Fibrous cap disruption is a definitive indicator of plaque vulnerability. Histologically unstable plaques also may be characterised by cap thickness, including e.g., a thin cap with a large lipid core. These plaques are known as 'thin-cap fibroatheroma' (TCFA) and typically have a cap thickness of 65 µm or less and a lipid core accounting for >40%, often >50% or >60%, of the plaque's total volume.

Importantly, cap thickness may not be uniform. Accordingly, in other embodiments, minimal cap thickness may be used as alternative parameter indicative of plaque vulnerability. In some embodiments the unstable plaque has a minimal cap thickness of 65 µm or less. That is, the thinnest part of the cap is 65 µm or less. Optical coherence tomography (OCT) systems may be used to measure minimal cap thickness.

In accordance with embodiments disclosed herein, an unstable plaque may be characterised by a cap thickness in a predetermined range of from about 0.01 to about 65 µm. For example, in various embodiments the minimum cap thickness may be 65 µm or less, 60 µm or less, 55 µm or less, 50 µm or less, 45 µm or less, 40 µm or less, 35 µm or less, 30 µm or less, 25 µm or less, 20 µm or less, 15 µm or less, 10 µm or less, 5 µm or less, or 1 µm or less.

In accordance with embodiments disclosed herein, an unstable plaque may be characterized by a cap to lesion ratio of about 80 or less. In one or more embodiments, a predetermined cap:lesion ratio is from about 10 to about 20. In one or more embodiments, the cap:lesion ratio of unstable plaque may be 75 or less, 70 or less, 65 or less, 60 or less, 55 or less, 50 or less, 45 or less, 40 or less, 35 or less, 30 or less, 25 or less, 20 or less, 15 or less, 10 or less, or 5 or less.

In accordance with embodiments disclosed herein, the contrast agent may provide delayed wash-out kinetics. Wash-out kinetics refers to the rate at which contrast enhanced signal intensity decreases after peak signal intensity is reached. Washout kinetics can be monitored by periodically calculating the Contrast to Noise Ratio (CNR). The CNR is the relationship of signal intensity differences between two regions, scaled to image noise.

$$\Delta CNR = CNR_{post\text{-}contrast} - CNR_{pre\text{-}contrast}$$

As disclosed herein, a change in the CNR before and after administering the contrast agent ($\Delta CNR$) can be used to identify unstable plaques.

In accordance with embodiments disclosed herein, a predetermined range for $\Delta CNR$ may be from about 1 to 80. In one or more embodiments, unstable plaque may have a $\Delta CNR$ of from about 10 to about 30, for example 10, 11, 12, 13, 14, 15, 16, 17, 18, 19, 20, 21, 22, 23, 24, 25, 25, 26, 27, 28, 29, 30. In various embodiments the $\Delta CNR$ for unstable plaque may be $\geq 5$, $\geq 10$, $\geq 15$, $\geq 20$, $\geq 25$, $\geq 30$, $\geq 40$, $\geq 50$, $\geq 60$, $\geq 70$ or $\geq 80$.

Without wishing to be bound by any particular theory, it is believed that during inflammatory processes that occur in atherosclerotic plaques MPO activates the contrast agent, which then forms dimers or oligomers and exhibits increased T1 relaxivity, protein binding and "trapping" in areas of high MPO activity, all leading to increased enhancement on T1-weighted MRI.

Accordingly, in one embodiment delayed wash-out kinetics in an unstable plaque refers to image enhancement of unstable plaque that is sustained over time. For example the image enhancement may be sustained for at least 10, 15, 20, 25, 30, 35, 40, 45, 50, 55, or 60 µminutes. In preferred embodiments, image enhancement indicative of unstable plaque is sustained for more than 30 µminutes, more than 45 µminutes, more than 60 µminutes.

Treatment Step: MPO Inhibitor

The methods disclosed herein may include the step of administering an MPO inhibitor. MPO inhibitors may reduce or inhibit MPO specific activity in unstable plaque. Accordingly, administration of an MPO inhibitor may be useful for both the polarization of established unstable plaque to a stable phenotype (see for example FIG. 14), or for the prevention or inhibition of unstable plaque formation. Accordingly, methods are also provided for the stabilisation of plaque and/or the inhibition of unstable plaque formation. The methods require administering an MPO inhibitor to a subject. In one embodiment a method for stabilising plaque comprises administering to a subject a therapeutically effective amount of an MPO inhibitor. The MPO inhibitor may be administered after the methods described herein have been used to detect (diagnose) the presence of unstable plaque, and diagnosis of unstable plaque by the methods described herein may then be repeated.

In accordance with preferred embodiments disclosed herein, an MPO inhibitor may be administered to a subject who has been identified as having, or being at risk of developing, unstable plaque. Such subjects may be identified by the methods for detecting or diagnosing unstable atherosclerotic plaque disclosed herein. Accordingly, a method for stabilising plaque, or for preventing or inhibiting unstable plaque formation may be performed after the detection/diagnostic methods disclosed herein.

It is contemplated that any MPO inhibitor may be useful in methods for the stabilisation of plaque or the prevention or inhibition of unstable plaque formation. Exemplary MPO inhibitors are known generally in the art and include, for example, thioxanthines and inhibitors disclosed in e.g., Tidén et al. J Biol Chem 2011; 286:37578-37589, and may be used in the methods described herein. Representative 2-thioxanthine MPO inhibitors include for example AZM198, 3-isobutyl-2-thioxo-7H-purin-6-one, 3-[(4-fluorophenyl)methyl]-2-thioxo-7H-purin-6-one, 3-(tetrahydrofuran-2-ylmethyl)-2-thioxo-7H-purin-6-one, 3-[[(2R)-tetrahydrofuran-2-yl]methyl]-2-thioxo-7H-purin-6-one, and 3-(2-methoxyethyl)-2-thioxo-7H-purin-6-one, AZD3241, 2-(6-(5-chloro-2-methoxyphenyl)-4-oxo-2-thioxo-3,4-dihydropyrimidin-1(2H)-yl)acetamide (also known as PF-06282999, see Ruggeri et al. J Med Chem 2015; 58:8513-8528), or PF-1355 (Zeng et al J Pharmacol Exp Ther 2015; 353:288-298), among others.

Administration of MPO Inhibitors

In accordance with the methods described herein an MPO inhibitor may be administered to a subject. The MPO inhibitor may be administered to atherosclerotic plaque in the subject. In some embodiments delivery is systemic and the MPO inhibitor is taken up into plaque. In some embodiments an MPO inhibitor is administered to the subject in an amount sufficient to inhibit extracellular MPO but not substantially inhibit intracellular MPO. The actual dose of the MPO inhibitor that is administered and/or the dosage regimen required to inhibit extracellular MPO but not substantially inhibit intracellular depends on a variety of factors, including the age, weight, sex, and medical condition of the subject, the severity and number of high-risk unstable atherosclerotic plaques detected by the methods, the route and frequency of administration, the particular MPO inhibitor employed, as well as the pharmacokinetic properties of the MPO inhibitor and thus may vary widely. The MPO inhibitor may be administered as often as necessary and for the period of time judged necessary by the treating physician, for example based on repeated imaging of unstable plaque by the methods described herein. One of skill in the art will appreciate that the dosage regime or amount of the MPO inhibitor to be administrated may need to be optimized for each individual. Those skilled in the art can determine an effective dose using information and routine methods known in the art.

In some embodiments the MPO inhibitor may be taken up by non-target cells, tissues or organs, but preferably does not have a significant negative effect on such cells or tissues, or on the subject as a whole.

Those skilled in the art will be able to select and use an appropriate route of administration based on their common general knowledge and information readily available to them, without undue experimentation.

MPO inhibitors may be administered as a formulation comprising a pharmaceutically effective amount of the MPO inhibitor, in association with one or more pharmaceutically acceptable excipients including carriers, vehicles and diluents. The term "excipient" herein means any substance, not itself a therapeutic agent, used as a diluent, adjuvant, or vehicle for delivery of a therapeutic agent to a subject or added to a pharmaceutical composition to improve its handling or storage properties or to permit or facilitate formation of a solid dosage form such as a tablet, capsule, or a solution or suspension suitable for oral, parenteral, intradermal, subcutaneous, or topical application. Excipients can include, by way of illustration and not limitation, diluents, disintegrants, binding agents, adhesives, wetting agents, polymers, lubricants, glidants, stabilizers, and substances added to mask or counteract a disagreeable taste or odor, flavors, dyes, fragrances, and substances added to improve appearance of the composition. Acceptable excipients include (but are not limited to) stearic acid, magnesium stearate, magnesium oxide, sodium and calcium salts of phosphoric and sulfuric acids, magnesium carbonate, talc, gelatin, acacia gum, sodium alginate, pectin, dextrin, mannitol, sorbitol, lactose, sucrose, starches, gelatin, cellulosic materials, such as cellulose esters of alkanoic acids and cellulose alkyl esters, low melting wax, cocoa butter or powder, polymers such as polyvinyl-pyrrolidone, polyvinyl alcohol, and polyethylene glycols, and other pharmaceutically acceptable materials. Examples of excipients and their use is described in Remington's Pharmaceutical Sciences, 20th Edition (Lippincott Williams & Wilkins, 2000). The choice of excipient will to a large extent depend on factors such as the particular mode of administration, the effect of the excipient on solubility and stability, and the nature of the dosage form.

The MPO inhibitor and pharmaceutical compositions may be formulated for oral, injectable, rectal, parenteral, subcutaneous, intravenous, topical, intravitreal or intramuscular delivery. Non-limiting examples of particular formulation types include tablets, capsules, caplets, powders, granules, injectables, ampoules, vials, ready-to-use solutions or suspensions, lyophilized materials and implants. Solid formulations such as the tablets or capsules may contain any number of suitable pharmaceutically acceptable excipients or carriers described above. MPO inhibitors may also be formulated for sustained delivery.

Tablets and capsules for oral administration may be in unit dose presentation form, and may contain conventional excipients such as binding agents, for example, acacia, gelatin, sorbitol, tragacanth, or polyvinylpyrrolidone; fillers, for example lactose, sugar, maize-starch, calcium phosphate, sorbitol or glycine; tabletting lubricants, for example, magnesium stearate, talc, polyethylene glycol or silica; disintegrants, for example, potato starch; or acceptable wetting agents such as sodium lauryl sulphate. The tablets may be coated according to methods well known in normal pharmaceutical practice.

Oral liquid preparations may be in the form of, for example, aqueous or oily suspensions, solutions, emulsions, syrups or elixirs, or may be presented as a dry product for reconstitution with water or other suitable vehicle before use. Such liquid preparations may contain conventional additives, such as suspending agents, for example, sorbitol, methyl cellulose, glucose syrup, gelatin, hydroxyethyl cellulose, carboxymethyl cellulose, aluminium stearate gel or hydrogenated edible fats, emulsifying agents, for example, lecithin, sorbitan monooleate, or acacia; non-aqueous vehicles (which may include edible oils), for example, almond oil, oily esters such as glycerin, propylene glycol, or ethyl alcohol; preservatives, for example, methyl or propyl p-hydroxybenzoate or sorbic acid; and, if desired, conventional flavouring or colouring agents.

For parenteral administration, including intravenous, intramuscular, subcutaneous, intravitreal, or intraperitoneal administration, fluid unit dosage forms may be prepared by combining the MPO inhibitor and a sterile vehicle, typically a sterile aqueous solution which is preferably isotonic with the blood of the recipient. Depending on the vehicle and concentration used, the compound may be either suspended or dissolved in the vehicle or other suitable solvent. In preparing solutions, the MPO inhibitor may be dissolved in water for injection and filter sterilized before filling into a suitable vial or ampoule and sealing. Advantageously, agents such as a local anaesthetic, preservative and buffering agents can be dissolved in the vehicle. To enhance the stability, the composition may be frozen after filling into the vial and the water removed under vacuum. The dry lyophilized powder may then be sealed in the vial and an accompanying vial of water for injection or other suitable liquid may be supplied to reconstitute the liquid prior to use. Parenteral suspensions are prepared in substantially the same manner except that the compound is suspended in the vehicle instead of being dissolved and sterilization cannot be accomplished by filtration. The MPO inhibitor can be sterilized by exposure to ethylene oxide before suspending in the sterile vehicle. A surfactant or wetting agent may be included in the composition to facilitate uniform distribution of the MPO inhibitor. In one or more preferred embodiments the MPO inhibitor is formulated as an injectable solution, suspension or emulsion.

Lyophilized formulations are preferably reconstituted with a solution consisting primarily of water (e.g., USP WFI, or water for injection) or bacteriostatic water (e.g., USP WFI with 0.9% benzyl alcohol). Alternatively, solutions comprising buffers and/or excipients and/or one or more pharmaceutically acceptable carriers may be used. The liquid that is to undergo freeze-drying or lyophilization preferably comprises all components desired in a final reconstituted liquid formulation.

In some embodiments, the composition comprising the MPO inhibitor is formulated in a sustained release formulation or depot. Exemplary sustained release formulations or depots include a microsphere; matrix; emulsion; lipid-based or polymer-based micelle or nanomicelle; nanovesicle such as a liposome, noisome, transfersome, discome, pharmacosome, emulsome or spanlastic, especially a liposome; microparticle, nanoparticle such as a nanocapsule or nanosphere composed of e.g., lipids, proteins, natural or synthetic polymers such as albumin, sodium alginate, chitosan, PLGA, PLA and/or polycaprolactone; or in situ gel such as an in situ hydrogel drug delivery system.

The amount of therapeutically effective MPO inhibitor that is administered and the dosage regimen for treating a disease condition with the compounds and/or pharmaceutical compositions of the present invention depends on a variety of factors, including the age, weight, sex, and medical condition of the subject, the severity of the plaque, the route and frequency of administration, the particular MPO inhibitor employed, as well as the pharmacokinetic properties (e.g., adsorption, distribution, metabolism, excretion) of the individual treated, and thus may vary widely. Such treatments may be administered as often as necessary and for the period of time judged necessary by the treating physician. One of skill in the art will appreciate that the dosage regime or therapeutically effective amount of the compound to be administrated may need to be optimized for each individual.

Generally, an effective dosage of the MPO inhibitor is expected to be in the range of about 0.0001 μmg to about 1000 μmg per kg body weight per 24 hours; typically, about 0.001 mg to about 750 μmg—per kg body weight per 24 hours; about 0.01 μmg to about 500 μmg per kg body weight per 24 hours; about 0.1 μmg to about 500 μmg per kg body weight per 24 hours; about 0.1 μmg to about 250 μmg per kg body weight per 24 hours; or about 1.0 μmg to about 250 μmg per kg body weight per 24 hours. More typically, an effective dose range is expected to be in the range of about 10 μmg to about 200 μmg 20 per kg body weight per 24 hours.

It will be apparent to one of ordinary skill in the art that the optimal quantity and spacing of individual dosages will be determined by the nature and extent of the plaques being-treated, the form, route and site of administration, and the nature of the particular individual being treated. Also, such optimum conditions can be determined by conventional techniques.

The MPO inhibitor may be administered along with a pharmaceutical carrier, diluent or excipient as described above. Alternatively, or in addition, the MPO inhibitor may be administered in combination with one or more other agents as part of a combination therapy.

The terms 'combination therapy' or 'adjunct therapy' in describing the use of a MPO inhibitor and one or more other pharmaceutical agents, are intended to embrace administration of each agent in a sequential manner in a regimen that will provide beneficial effects of the drug combination, and is also intended to embrace co-administration of such agents in a substantially simultaneous manner, such as in a single formulation having a fixed ratio of these active agents, or in multiple, separate formulations of each agent.

In accordance with various embodiments of the present invention one or more MPO inhibitors may be formulated or administered in combination with one or more other therapeutic agents. Thus, in accordance with various embodiments of the present invention, one or more MPO inhibitors may be included in combination treatment regimens with surgery and/or other known treatments or therapeutic agents, and/or adjuvant or prophylactic agents.

A number of agents are available in commercial use, in clinical evaluation and in pre-clinical development, which could be selected for treatment or prevention of atherosclerosis. Suitable agents which may be used in combination therapy will be recognized by those of skill in the art. Suitable agents are listed, for example, in the Merck Index, *An Encyclopaedia of Chemicals, Drugs and Biologicals,* 15$^{th}$ Ed (2013), ISBN 978-1-84973670-1, the entire contents of which are incorporated herein by reference.

For example, when used in the treatment of atherosclerotic plaque, MPO inhibitors may be administered with an additional agent, or combinations thereof, such as: statins (e.g., atorvastatin, fluvastatin, lovastatin, pitavastatin, pravastatin, rosuvastatin calcium, simvastatin), ACE inhibitors, blood thinners (e.g., aspirin, clopidogrel, ticagrelor, prasugrel), fibrates (e.g. gemfibrozil, fenofibrate), and PCSk9 inhibitors.

Combination regimens may involve the active agents being administered together, sequentially, or spaced apart as appropriate in each case. Combinations of active agents including compounds of the invention may be synergistic.

The efficacy of a treatment regime may also be evaluated by determining the level of expression of MPO in a plaque of a subject treated with an MPO inhibitor. After a period of treatment the level of expression of MPO in a plaque of the subject is determined (for example using the MRI based methods disclosed herein) and a change in the level of MPO activity is indicative of the efficacy of the treatment regime.

Advantageously, the technology disclosed herein provides a non-invasive method for detecting or identifying increased MPO activity in unstable plaque that may be used as a diagnostic tool for detecting unstable atherosclerotic plaque, which is a prognostically significant indicator of the increased likelihood of adverse cardiac events, such as myocardial infarction and coronary artery disease. An imaging strategy using MPO-activated MRI contrast agents disclosed herein, such as MPO-Gd or similar MPO contrast agents, has several advantages. Firstly, such a contrast agent would be effective for coronary imaging, as it is not constrained by background uptake in the surrounding myocardium. Secondly, as the contrast agent is enzymatically activated, it provides a direct index of disease activity and thus has utility in identifying high-risk (unstable) plaque. Finally, unlike other contrast agents used to image atherosclerosis, MPO-activated MRI contrast agents such as MPO-Gd allows for the direct localisation and quantification of a potential therapeutic target, which may be used to guide administration of MPO inhibitors or other therapies that modulate inflammation.

Embodiments of the invention will now be discussed in more detail with reference to specific examples which are provided for exemplification only and which should not be considered as limiting the scope of the invention in any way.

EXAMPLE 1

Methods

All experiments were approved by the relevant Animal Ethics Committees. Numeric data was analysed for normality using the Shapiro-Wilk normality test, the significance determined using the appropriate parametric or non-parametric test, and individual data then shown with mean±SD.

Animals

Male apolipoprotein E gene-deficient (Apoe$^{-/-}$) mice, obtained originally from the Animal Resource Centre in Western Australia, were bred in the BioCORE facility at the Victor Chang Cardiac Research Institute. Myeloperoxidase gene-deficient (Mpo$^{-/-}$) mice on a C57BL/6J background were derived originally from Prof. A. J. Lusis (UCLA, Los Angeles, CA)1 and obtained from Prof. S. R. Holdsworth (Monash University, Melbourne, VIC, Australia). These mice were crossed with Apoe$^{-/-}$ mice to yield Mpo$^{-/-}$Apoe$^{-/-}$ mice. Mice (6 weeks of age) were fed Western Diet (WD) containing 22% fat and 0.15% cholesterol (SF00-219, Specialty Feeds, Western Australia) for a total of 13 weeks.

Six weeks after commencement of WD, tandem stenosis (TS) was introduced into the mice as described below.

The Animal Ethics Committees of the Garvan Institute of Medical Research/St Vincent's Hospital and the University of New South Wales approved all experiments.

AZM198 Treatment

Figure 1:
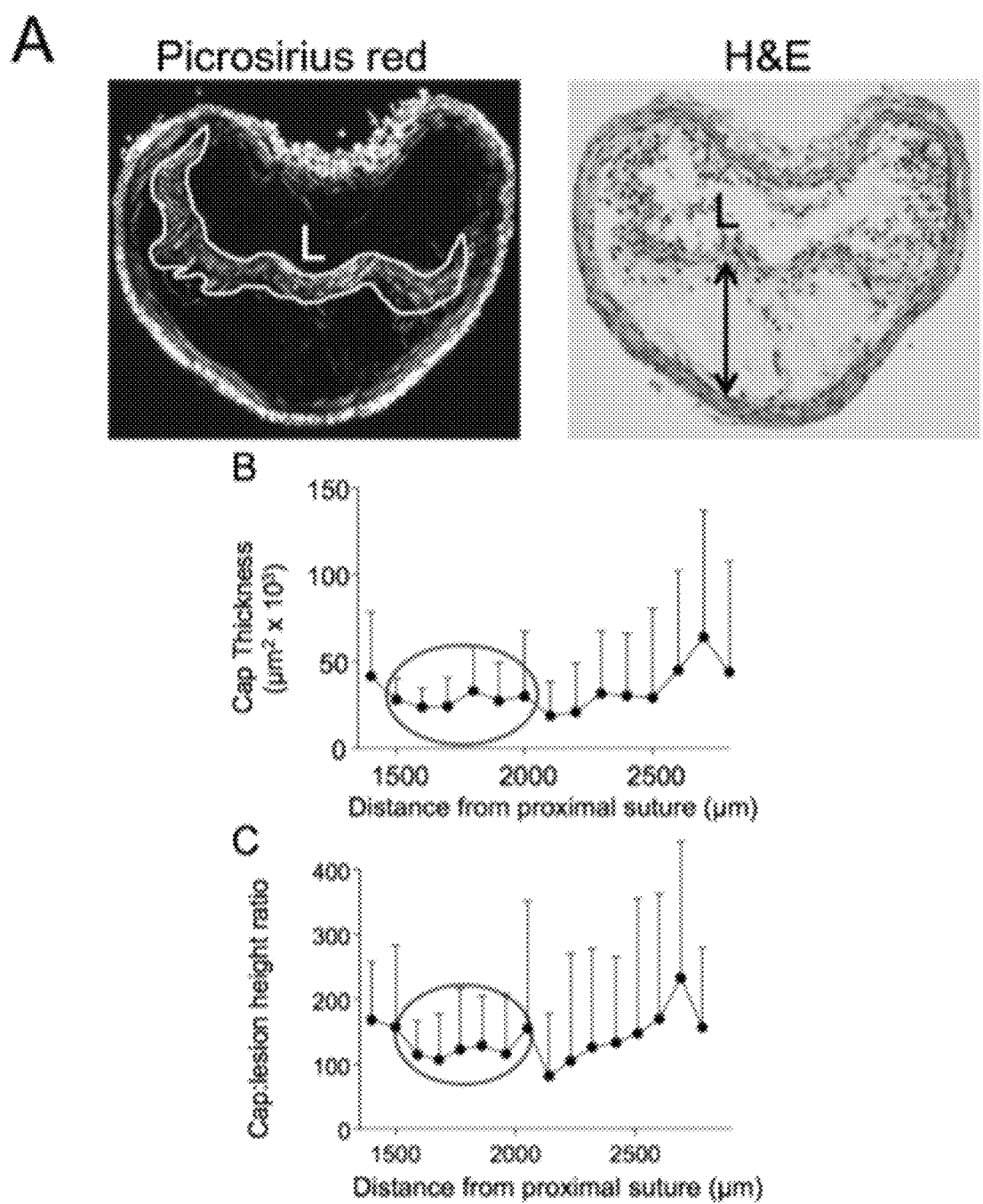
FIG. 1. Assessment of fibrous cap thickness in plaque with unstable phenotype of TS mice. A, Picrosirius red (left) and haematoxylin and eosin (H&E) staining (right) of plaque with unstable phenotype in the right carotid artery. Cap thickness was determined as the area of picrosirius red stained cap viewed under polarised light showing the fibrous cap (yellow line). Lesion height was determined from H&E stained sections (arrow). L=lumen. B, Fibrous cap thickness and C, cap-to-lesion height ratio in unstable plaque. In an initial pilot study, we sectioned the entire area (~3,000 μm) prone to vulnerable plaque in the right carotid artery at 100 μm intervals from the proximal suture. We observed most consistent values for cap thickness and cap:lesion height ratios between 1,500-2,000 μm proximal to the proximal suture (B and C). Data shown are mean±SD, n=10. D, Measurement of fibrous cap thickness (arrow) by Optical Coherence Tomography.
Figure 1:
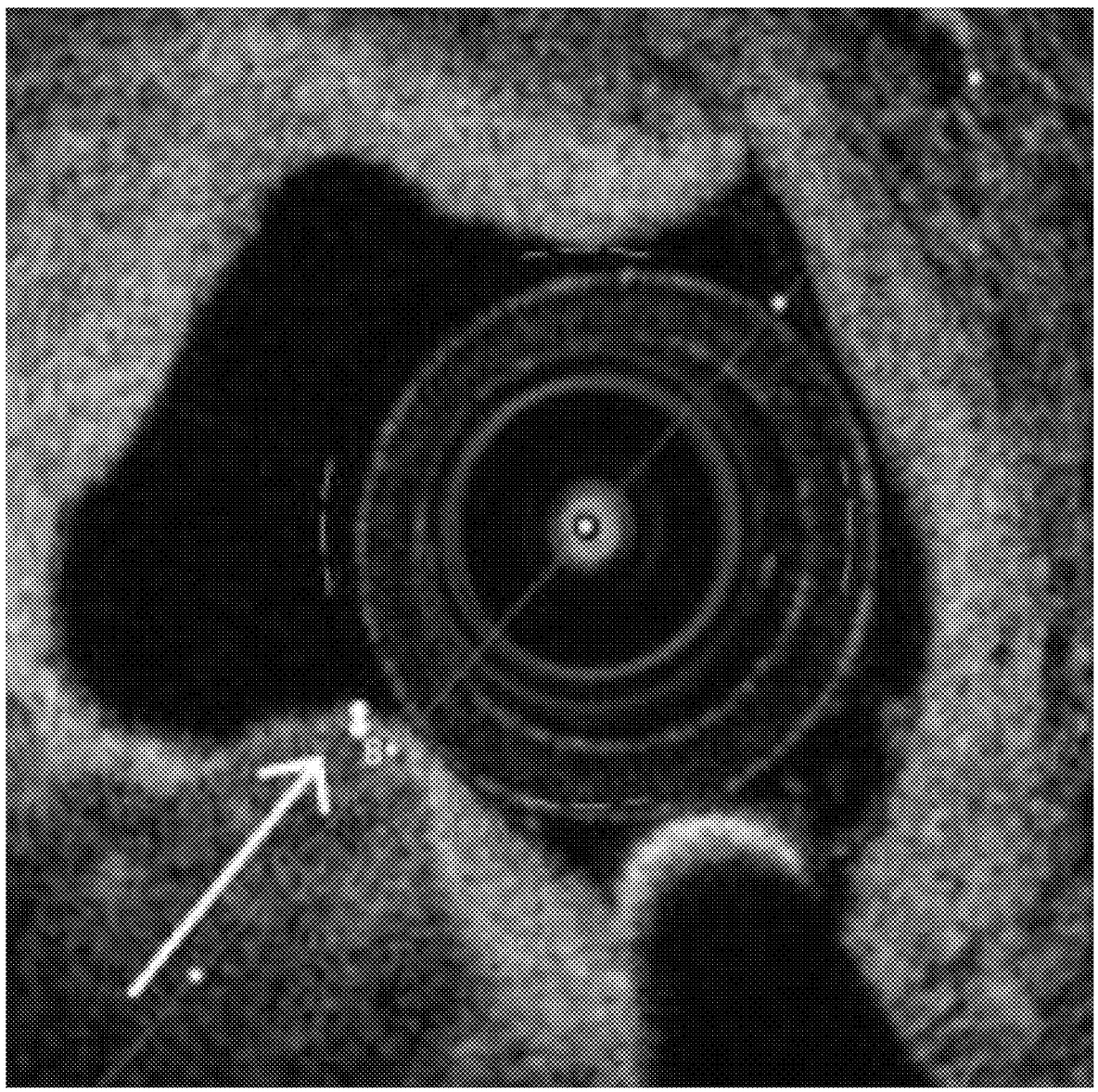

For pharmacological inhibition of MPO, AZM198 (AstraZeneca, Sweden) was administered by incorporation into WD at a daily dose of 500 μmol/kg bodyweight based on an average daily food consumption of ~3.7 g per mouse. This yielded a total plasma concentration of AZM198 of ~2 μM, corresponding to a free concentration of 0.6 μM·2 Based on the potency of human MPO purified from HL60 cells (ascorbate oxidation) and iodination by human thyroid peroxidase expressed by transfected insect cells, this concentration corresponds to 98% inhibition of MPO activity and a marginal (8%) inhibition of thyroid peroxidase (FIG. 1). In contrast, intracellular MPO inhibition (as assessed by intragranular MPO activity in purified neutrophils) was predicted to require substantially higher concentrations of AZM198. In the experiments disclosed herein, residual MPO activity was observed in AZM198-treated mice (20-40% depending on the methodology employed), in contrast to $Mpo^{-/-}$ mice. Thus, some of the MPO activity quantified in plaque with unstable phenotype may represent intracellular MPO in actively phagocytosing neutrophils and/or macrophages.

Tandem stenosis (TS) surgery Six weeks after commencement of WD, male $Apoe^{-/-}$ mice were anaesthetised with 4% isoflurane. An incision was made in the neck and the right common carotid artery was dissected from circumferential connective tissues. Two stenoses with 150 μm outer diameter were placed with the distal stenosis 1 μmm from the carotid artery bifurcation and the proximal stenosis 3 μmm from the distal stenosis. To control for the extent of constriction caused by the stenosis, a 150-μm needle (Ethicon 8-0, Virgin silk blue, W1782) was placed on top of the exposed right common carotid artery before a 6-0 blue-braided polyester fiber suture (TICRON 0.7 Metric) was tied around both the artery and needle, and the needle then removed. Blood flow was measured before and after the addition of each ligature using a perivascular flow module (Transonic, TS420) and a 0.7 μmm perivascular flow probe (Transonic MA0.7PSB). Flow for each ligature in the TS was defined as 70% of baseline flow after addition of the distal ligature and 20% of baseline flow after addition of the proximal ligature. Animals were euthanised 7 weeks after surgery by cardiac puncture and exsanguination. At this time, the segment proximal to the proximal suture in the right common carotid artery (referred to as "Segment I" in Circ Res. 2012; 113:252-265) contains plaque with unstable phenotype characterised by consistent thinning of the fibrous cap, abundant inflammatory cells, occasional neovessels, cap disruption and intraplaque haemorrhage, as well as luminal thrombus of fibrin and platelets. In contrast, the brachiocephalic trunk contains a thick cap and abundance of collagen in the atheroma area, features of a stable plaque.

The brachiocephalic artery was chosen as a site of "stable" plaque because: (i) MR imaging at this site can be acquired simultaneously with plaque with unstable phenotype and normal vessel wall in the right and left common carotid arteries, respectively; (ii) the brachiocephalic artery is commonly used for atherosclerosis studies in $Apoe^{-/-}$ mice with lesions in this vessel being stable; and (iii) computational fluid dynamics demonstrate no significant reduction in vessel wall shear stress in this region following TS surgery.

Assessment of MPO activity Measurement of in vivo and ex vivo MPO activity followed the procedure described in Talib et al (Free Radic Biol Med 2016; 97:124-135). In brief, for ex vivo MPO-activity, tissue was homogenised in PBS containing 0.05 M diethylenetriaminepentaacetic acid (DTPA) and 1 Roche Complete™ (169749800) protease inhibitor.

Following homogenisation, tissue was incubated with glucose (20 μmg/mL) and glucose oxidase (40 μg/mL) in the presence of 20 μmM Trolox® and 50 μM hydroethidine (HE, Tyger Scientific, Ewing, NJ) for 30 μmin at 37° C. in the dark. Hydroethidine and its oxidation products were then extracted by the addition of 80% ethanol containing 3 μM 2-chloroethidium-d5 prior to LC-MS/MS analysis as previously described (Free Radic Biol Med 2016; 97:124-135). In vivo MPO activity was determined following administration of 80 μL 20 μmM HE dissolved in a 1:1 solution of dimethylsulfoxide:saline (vol/vol) to mice via retro-orbital injection 45 μmin before euthanasia. Tissue was collected and homogenised in 80% ethanol containing 0.4 nM 2-chloroethidium-d5 prior to measurement of HE and its products using LC-MS/MS as previously described (Free Radic Biol Med 2016; 97:124-135).

Magnetic Resonance Imaging

At 7 weeks following TS surgery, isoflurane-anaesthetised mice were imaged in the prone position using a 9.4T Bruker Biospec 94/20 Avance III system (Bruker, Ettlingen, Germany) with a 50-mm quadrature radiofrequency coil and respiratory-gated image acquisition. Mice were imaged before and after intravenous administration of 0.3 μmmol/kg of the MPO sensor bis-5-hydroxytryptamide-DTPA Gd (MPO-Gd) or DTPA-Gd (Magnevist, Bayer, Leverkusen, Germany) via a tail vein catheter. Prior to contrast injection, a flow-compensated 2D-FLASH time-of-flight (TOF) angiography in a coronal slice orientation was performed to assess intra-vessel (luminal) volume and geometry using a flow compensated 2D-GRE sequence (FLASH) for time-of-flight (TOF) angiography in an axial slice orientation with the following major parameters: TR 34 μms, TE 3 μms, slice thickness 0.5 μmm, interslice distance 0.35 μmm, 40 slices, matrix size 128×128, FOV 20×20 μmm, in-plane resolution 156×156 μm. This was followed by a T1-weighted fast spin echo (TurboRARE, T1-TSE) acquired in the same orientation with the following parameters: TR 1500 μms, TE 8.5 μms, ETL 8, slice thickness 1 μmm, FOV 20×20 μmm, matrix size 192×192, in-plane resolution 104×104 μm. This T1-TSE protocol was then repeated in a scan series covering a period of one hour following contrast injection to assess contrast agent inflow and retention. OsiriX (Version 7.0, Pixmeo, Switzerland) was used for image analysis. In T1-TSE images, separate regions of interest were assigned to the vessel wall, skeletal muscle (reference) and background (air). The contrast-to-noise ratio (CNR) was calculated as follows: $CNR=(SI_{vessel\ wall}-SI_{skeletal\ muscle})/SD_{background}$ The mean CNRs of three consecutive slices in plaque with unstable phenotype and corresponding segments of the left carotid artery (plaque-free), in addition to 1-2 consecutive slices in the brachiocephalic trunk (stable plaque, SP), were calculated. Segmental enhancement attributable to MPO was assessed by calculating the $\Delta CNR=CNR_{post-contrast}-CNR_{pre-contrast}$.

Tissue Collection

At the end of the intervention or after scanning, mice were killed by exsanguination whilst anaesthetised with isoflurane. Blood was collected by cardiac puncture into a heparin-coated 1 μmL syringe using a 25-gauge needle, and the animal then perfused with phosphate buffered saline administered under physiological pressure. Blood was centrifuged (2,000 g, 15 μmin, 4° C.), plasma collected and snap frozen on dry ice before being stored at −80° C. The left and right common carotid arteries, brachiocephalic trunk, and heart were cleared of surrounding adipose and connective tissue before being excised, snap frozen on dry ice and stored at −80° C. for subsequent assessment of MPO activity or histology and immunohistochemistry. The left and right carotid arteries were embedded in optimal cutting temperature compound for cryosectioning and serially sectioned using a cryostat set to a thickness of 6 μm (for histology and immunohistochemistry) or 16 μm (Gd analysis by nuclear microscopy).

Histology

In a pilot study, the entire 3 μmm long carotid artery segment proximal to the proximal suture in unstable plaque (previously referred to as "Segment I") was sectioned at 100 μm intervals. 6 sections per interval were obtained for representation. Fibrous cap thickness was defined by calculated positive birefringence area under polarised light in picrosirius red staining (FIG. 2A). Lesion height was defined by the maximal distance from the vessel wall to the lumen in the plaque region (FIG. 2, H/E stain). We observed most consistent values for cap thickness (FIG. 2B) and cap:lesion height ratios between 1,500-2,000 μm proximal to the proximal suture (FIG. 2C). For all subsequent studies, therefore, serial cryosections were obtained at 100 μm intervals at 1,500-2,000 μm proximal to the proximal suture in the right common carotid artery, and from the brachiocephalic trunk.

Sections were stored at −20° C. until staining was performed. Picrosirius red staining was performed to visualise collagen within atherosclerotic plaque in the right common carotid artery (1,500 μm proximal to the proximal suture), as described previously (Circ Res. 2013; 113:252-265). Briefly, frozen sections were fixed in 10% neutral buffered formalin, washed, stained for 1 h in picrosirius red solution [0.6% w/v of Direct red (Sigma Cat #365548) in saturated picric acid], differentiated in 0.1 M HCl, dehydrated and covered with coverslips using DPX mounting media. Martius Scarlet Blue staining was used to visualise fibrin.5 Haemosiderin was detected using the Prussian Blue staining kit (Polysciences Cat #24199) to visualise stored iron. Haematoxylin and eosin staining was used for histomorphometry of aortic sinus and plaque burden, and for morphology to accompany the metal analysis. Images were obtained using a Leica Brightfield microscope. All histological data analyses were performed by an operator blinded to animal genotype or treatment.

Immunohistochemistry

The left and right common carotid arteries and brachiocephalic trunk were sectioned as described above. Sections were incubated in primary antibody [rat anti-mouse Ter-119 biotin (eBioscience 13 5921) 1:400; rabbit polyclonal anti-myeloperoxidase (Abcam ab9535) 1:50; and anti-smooth muscle actin antibody (ProteinTech 23081-1-AP) 1:200; anti-haemoglobin subunit alpha antibody (Abcam ab102758) 1:100; goat polyclonal anti-monocyte chemoattractant protein-1 (R&D systems AF-479) 1:100; and rat anti mouse macrophages/monocytes antibody (Bio-red MCA519) 1:100] at 4° C. overnight. After the wash steps and incubation in ABC reagent, DAB reagent was applied to each section. Conversion of the DAB substrate to a coloured product was monitored and slides were immersed in dH2O to stop the reaction. Sections were dehydrated and covered with coverslips using DPX mounting media. Images were obtained using a light microscope (Leica Brightfield or Olympus BX50 μmicroscope), and staining intensities quantified using ImageJ (for MPO staining) or Optimas (for all other markers). Each IHC protein marker, except MPO, was determined in at least three sections of atherosclerotic plaques obtained from each animal and taken between 1,500-2,000 μm (see FIG. 1). For MPO, one section per mouse, taken between 1,500-2,000 μm, was used. The amount of protein present was quantified by an operator blinded to animal genotype or treatment, using Optimas 6.2 VideoPro-32 (or ImageJ). Results were expressed as a percentage of stained area over total plaque area, and the data shown for each animal and with means±SD indicated.

Blood Lipid Analysis

Total plasma cholesterol, LDL- and HDL-cholesterol, and triglyceride concentrations were measured as described previously (Circ Res. 2013; 113:252-265) with the Cobas Integra® 400 plus autoanalyser using the following standard commercial enzymatic assay kits from Roche Diagnostics (Germany): cholesterol Gen.2, HDL cholesterol plus 2nd generation, LDL-cholesterol plus 2nd generation, and triglycerides. Colorimetric changes were measured at 512 nm for total cholesterol and triglycerides, or at 583 nm for HDL- and LDL-cholesterol.

Nuclear Microscopy

Nuclear microscopy experiments were performed at the Centre for Ion Beam Applications at the National University of Singapore, as described previously.6 Briefly, the samples were mounted onto a 3-axis stage within a scattering chamber maintained at <5×10−6 μmbar. A collimated proton beam (H+) at 2.1 MeV was generated using a 3.5 MV Singletron accelerator and kept incident onto the samples inclined at 45 degrees to the incident beam. The broad incident ion beam was focused down to a spot size of 1 μm and scanned across the region of interest. Data was acquired simultaneously using a combination of three ion beam analytical techniques namely proton induced X-ray emission (PIXE), Rutherford backscattering spectroscopy (RBS), and scanning transmission ion microscopy (STIM).

PIXE data was collected using a Si(Li) detector placed at 20 μmm from the samples to the Si(Li) crystal face. RBS and STIM data were measured by a passivated implanted planar silicon (PIPS) detector. The RBS detector was mounted at a back scattering angle of 160 degrees to the incident beam and the STIM detector was mounted at a forward angle of 20 degrees off-axis to the incident beam to collect the forward scattered proton beam that has undergone a small fraction of energy loss after passing through the thin biological samples.

Scanning transmission ion microscopy provides structural maps based on the energy lost by the protons as they pass through the relatively thin organic samples with thicknesses of 30 μm or less, enabling structural identification without fixing or staining. Trace elemental mapping was performed using particle-induced X-ray emission, which simultaneously provides multiple elements with high quantitative accuracy and sensitivity to a few parts per million in biological materials. Rutherford backscattering spectroscopy was used to measure the information on the sample thickness and matrix composition as well as calculating the charge that reflects the interactions between beam and samples. The obtained PIXE spectra were fitted using GUPIXWIN7 and the RBS spectra were fitted in SIMNRA. To examine the spatial resolution of Gd, higher resolution scans were carried out after the initial acquisition (680 μm scan size).

Statistical Analysis

All numeric data were first analysed for normality using the Shapiro-Wilk normality test, with significance determined subsequently using the appropriate parametric or non-parametric test. The CNR for MPO-Gd-treated and DTPA-Gd-treated arteries were analysed using unpaired T-test to determine differences in retention of the MRI contrast agent. Differences in DCNR, MPO activity and histological analyses between TS Apoe$^{-/-}$ and Mpo$^{-/-}$Apoe$^{-/-}$, or between TS Apoe$^{-/-}$ fed WD±AZM198 were assessed using the Mann-Whitney rank sum test, or unpaired T-test where appropriate.

All statistical analyses were performed with GraphPad Prism version 7.0d for Mac (GraphPad Software, La Jolla California USA) and individual data shown with mean±SD.

Results

The TS mouse model of plaque instability reflects human atherosclerotic plaque instability, including consistent thinning of the fibrous cap with occasional cap disruption and intraplaque haemorrhage. This model also represents a discovery tool for the development and testing of therapeutic strategies aimed at preventing plaque rupture.

MPO Activity is Higher in Plaque with Unstable than Stable Phenotype

Figure 3:
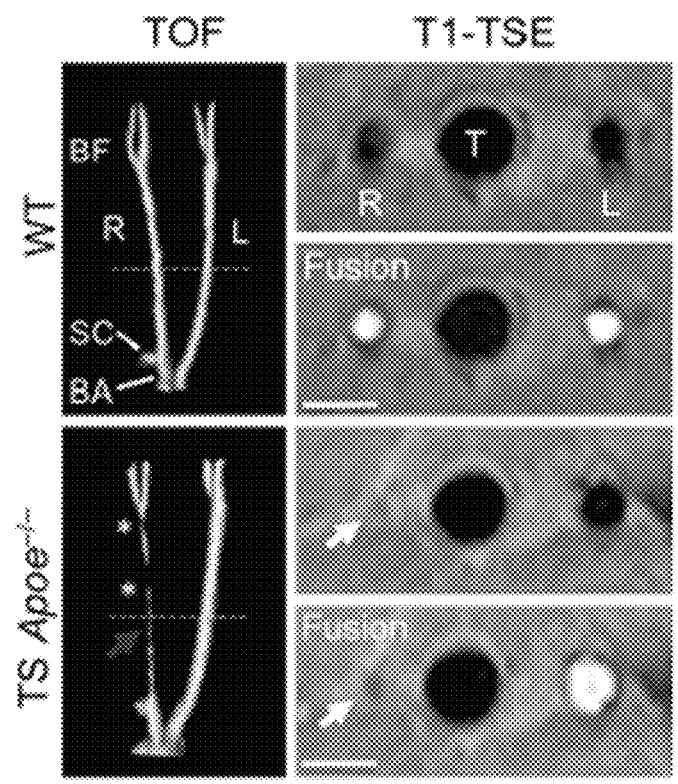
FIG. 3. MPO-Gd selectively enhances unstable atherosclerotic plaque that contains higher MPO activity than stable plaque. A, Time-of-flight angiography (TOF, 3D rendered) of the right (R) and left (L) carotid arteries, the carotid bifurcation (BF), subclavian (SC) and brachiocephalic arteries (BA) in a wild-type (WT) and TS Apoe$^{-/-}$ mouse after 13 weeks of Western Diet (WD), with corresponding (broken line) cross-sectional T1-weighted turbo spin echo (T1-TSE) images. Asterisks indicate the tandem stenosis while red arrow depicts the site of unstable plaque with reduced signal due to luminal stenosis and reduced blood flow (visualised with TOF/T1-TSE fusion). B, Pre- and post-Mpo-Gd and DTPA-Gd T1-TSE imaging in TS Apoe$^{-/-}$ mice. Representative as-acquired (2-cm field-of-view) MR images and higher-magnification images of unstable plaque (R), plaque-free artery (L) and stable plaque (BA) before and 60 μmin after administration of MRI contrast agent, with corresponding time-course of CNR (Contrast to noise ratio), (MPO-Gd, filled symbols; DTPA-Gd, open symbols) in L (squares), R (circles) and BA (triangles). Broken rectangles and circles indicate areas of interest for vessel wall and skeletal muscle, respectively; Scale bar=1 μmm. Data show mean±SD of n=6 (Mpo-Gd) and n=5 (DTPA-Gd) separate experiments with difference at 60 μmin post-contrast assessed by unpaired t-test. C, Quantification of tissue gadolinium (Gd) and phosphorus (P) by nuclear microscopy in unstable plaque following administration of MPO-Gd (circles) or DTPA-Gd (squares). Corresponding H&E sections indicate the arterial lumen (L). D, In vivo and E, ex vivo MPO activity in unstable and stable plaque of TS Apoe$^{-/-}$ mice after 13 weeks of WD. MPO activity was assessed by the conversion of hydroethidine to 2-chloroethidium (2-CI-E+) determined by LC-MS/MS as described in Methods. Results show individual values of separate experiments with mean+SD.
Figure 3:
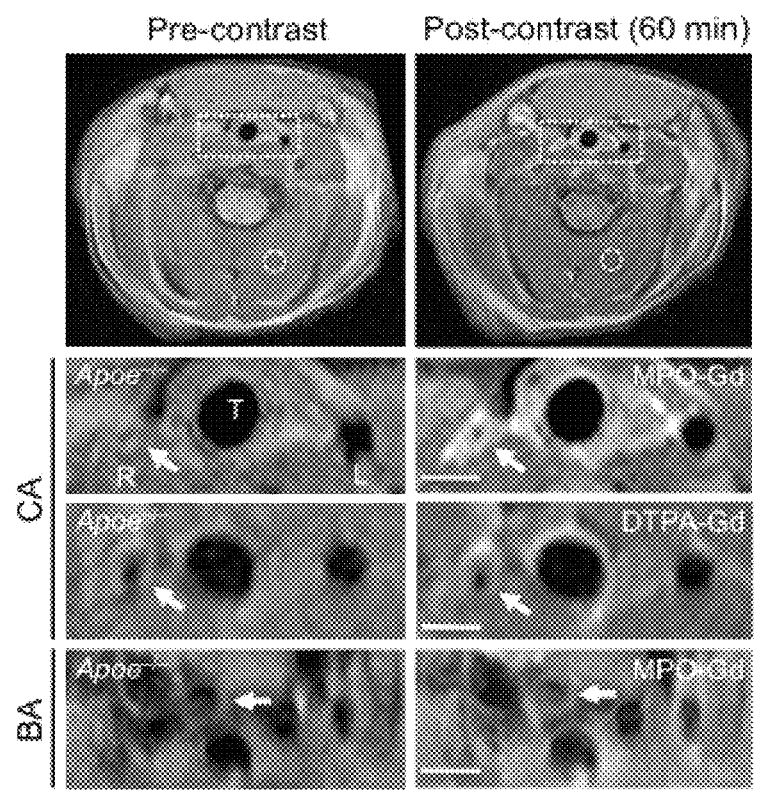
Figure 3:
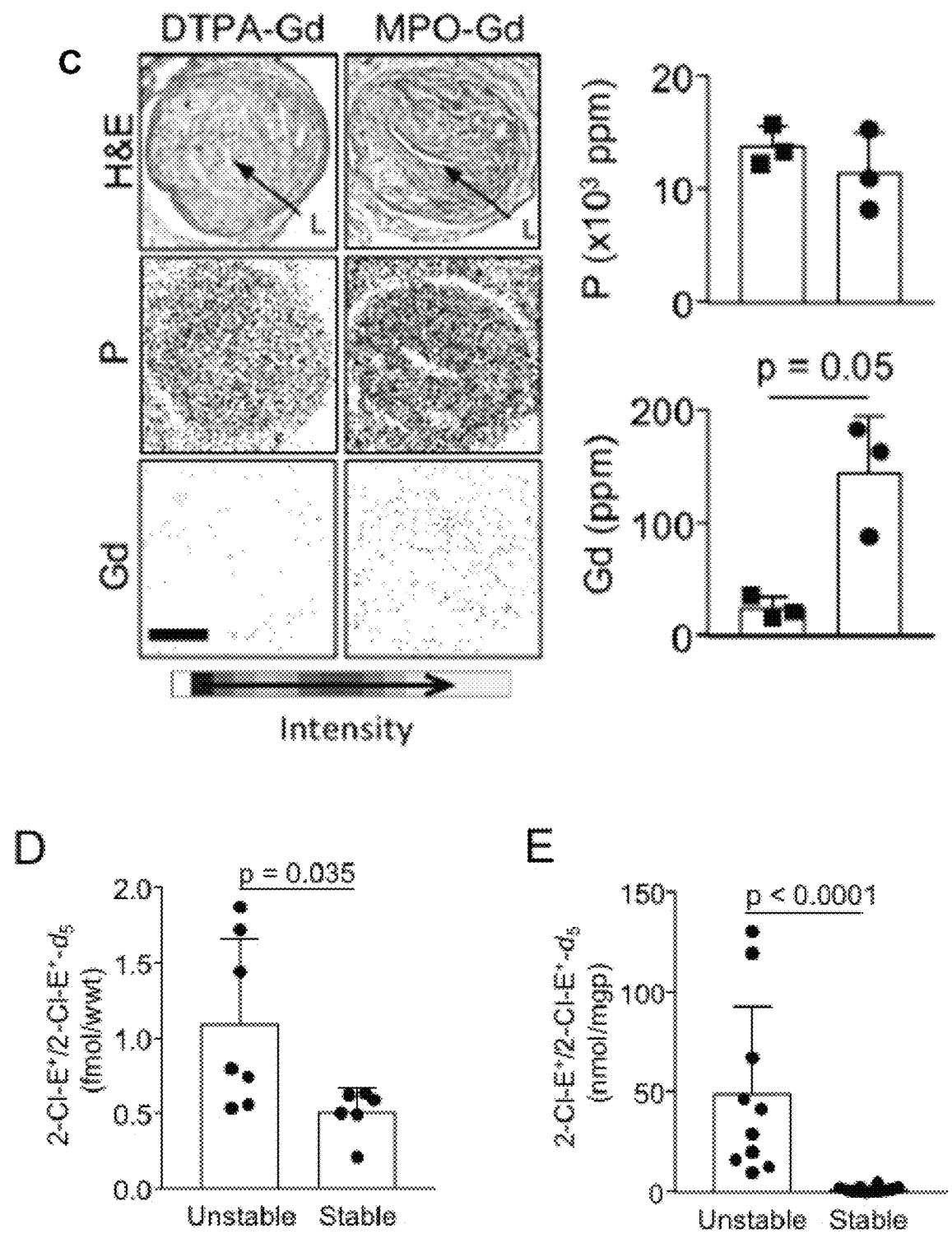

The inventors employed MPO-Gd and T1-weighted turbo spin echo imaging (T1-TSE) (FIG. 2) to assess MPO activity in unstable and stable atherosclerotic plaques in TS Apoe$^{-/-}$ mice. Time-of-flight (TOF) angiography showed decreased signal in the right common carotid artery at the site of unstable plaque due to luminal stenosis and decreased arterial flow, whereas the angiographic appearance of the brachiocephalic artery that contained stable plaque was unchanged compared with WT mice (FIG. 3A). The latter was ascribed to preservation of blood flow via the subclavian artery, as predicted by computational fluid dynamics, effectively shielding the brachiocephalic artery from alterations in shear stress following TS surgery. For contrast-enhanced imaging, 0.3 µmmol/kg MPO-Gd or DTPA-Gd was administered intravenously following acquisition of baseline MRI sequences (FIG. 2B).

There was no significant enhancement of the non-diseased vessel wall of the left carotid artery following administration of MPO-Gd (FIG. 3B). In contrast, administration of MPO-Gd resulted in enhancement of unstable plaque in the right carotid artery at 30 µmin after contrast injection (CNR=23.7±6.8, mean±SD), which was sustained at 60 µmin (CNR=25±6.4) (FIG. 3B, right), consistent with activation and retention of this MRI contrast agent in unstable plaque. Administration of DTPA-Gd, a contrast agent with no molecular specificity, resulted in enhancement of unstable plaque on T1-weighted imaging at 30 µmin following injection (CNR=19.2±7.2), which decreased at 60 µmin (CNR=13.4±3.6) (FIG. 3B), consistent with movement into and out of the extracellular space of atherosclerotic plaque. In unstable plaque, administration of MPO-Gd did not result in significant sustained enhancement of the brachiocephalic artery that contains stable plaque (FIG. 3B). Determination of plaque Gd content by nuclear microscopy confirmed significant accumulation of Gd in unstable plaque following administration of MPO-Gd compared with DTPA-Gd (FIG. 3C).

The inventors next assessed MPO activity by quantifying the MPO-specific conversion of hydroethidine (administered in vivo or ex vivo) to 2-chloroethidium, determined by liquid chromatography with tandem mass spectrometry (LC-MS/MS). MPO activity, both in vivo (FIG. 3D) and ex vivo (FIG. 3E), was significantly higher in unstable than stable plaque. Overall, the results of the MPO-Gd MRI and hydroethidium LC-MS/MS studies suggest that thresholds of MPO activity measured with non-invasive imaging may be used to delineate unstable from stable plaques.

Figure 4:
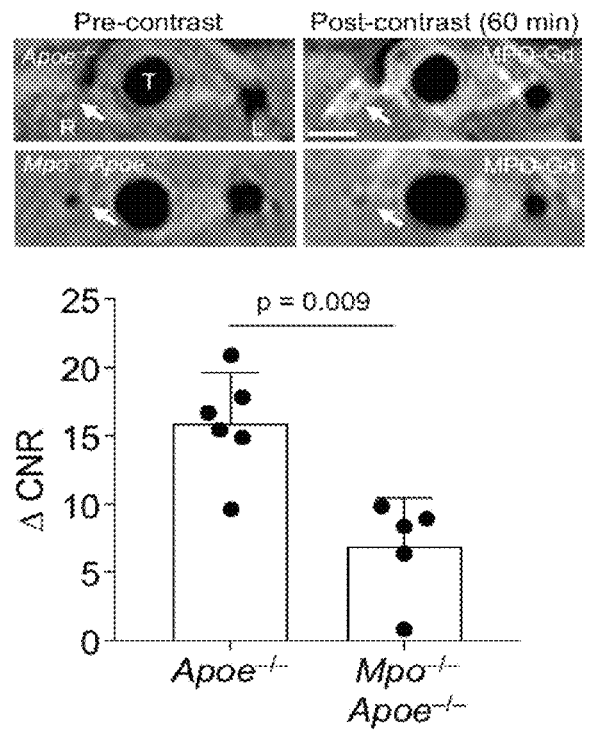
FIG. 4. Deletion of MPO increases fibrous cap thickness in unstable plaque. A, T1-TSE images of the right (R) and left (L) carotid arteries before and 60 μmin post administration of MPO-Gd (0.3 μmmol/kg) to TS Apoe$^{-/-}$ and TS Mpo$^{-/-}$Apoe$^{-/-}$ mice with corresponding ΔCNR data. B, Representative picrosirius red stained sections of unstable plaque in the right carotid artery viewed under polarised light (left) and bright field (right) from TS Apoe$^{-/-}$ and TS Mpo$^{-/-}$Apoe$^{-/-}$ mice fed WD for 13 weeks. Scale bar=100 μm. C, Average fibrous cap thickness and (D) cap:lesion height ratio in TS Apoe$^{-/-}$ versus TS Mpo$^{-/-}$Apoe$^{-/-}$ mice at the end of the 13 weeks study. Data show individual values with mean+SD analyzed by Mann-Whitney rank sum test. L=lumen. T=trachea.
Figure 4:
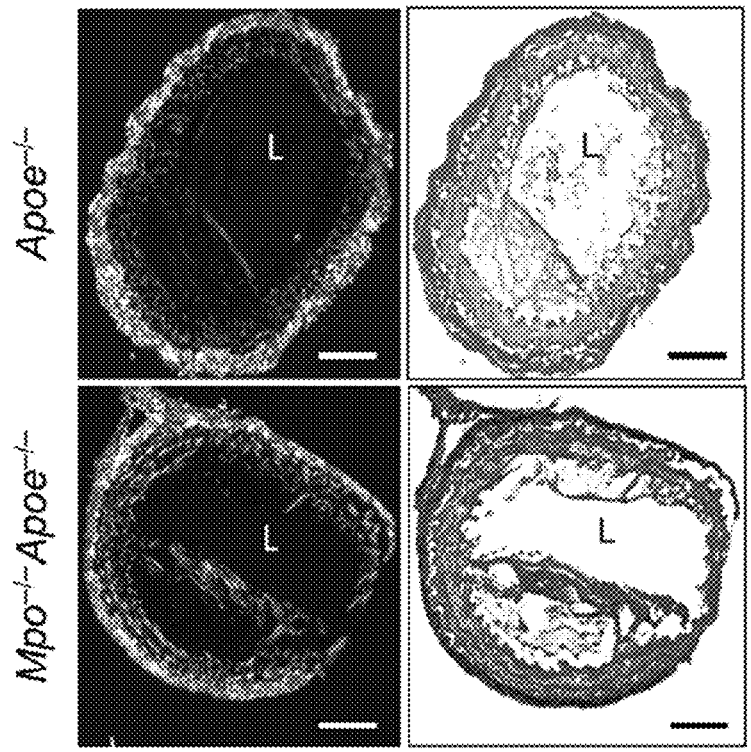
Figure 4:
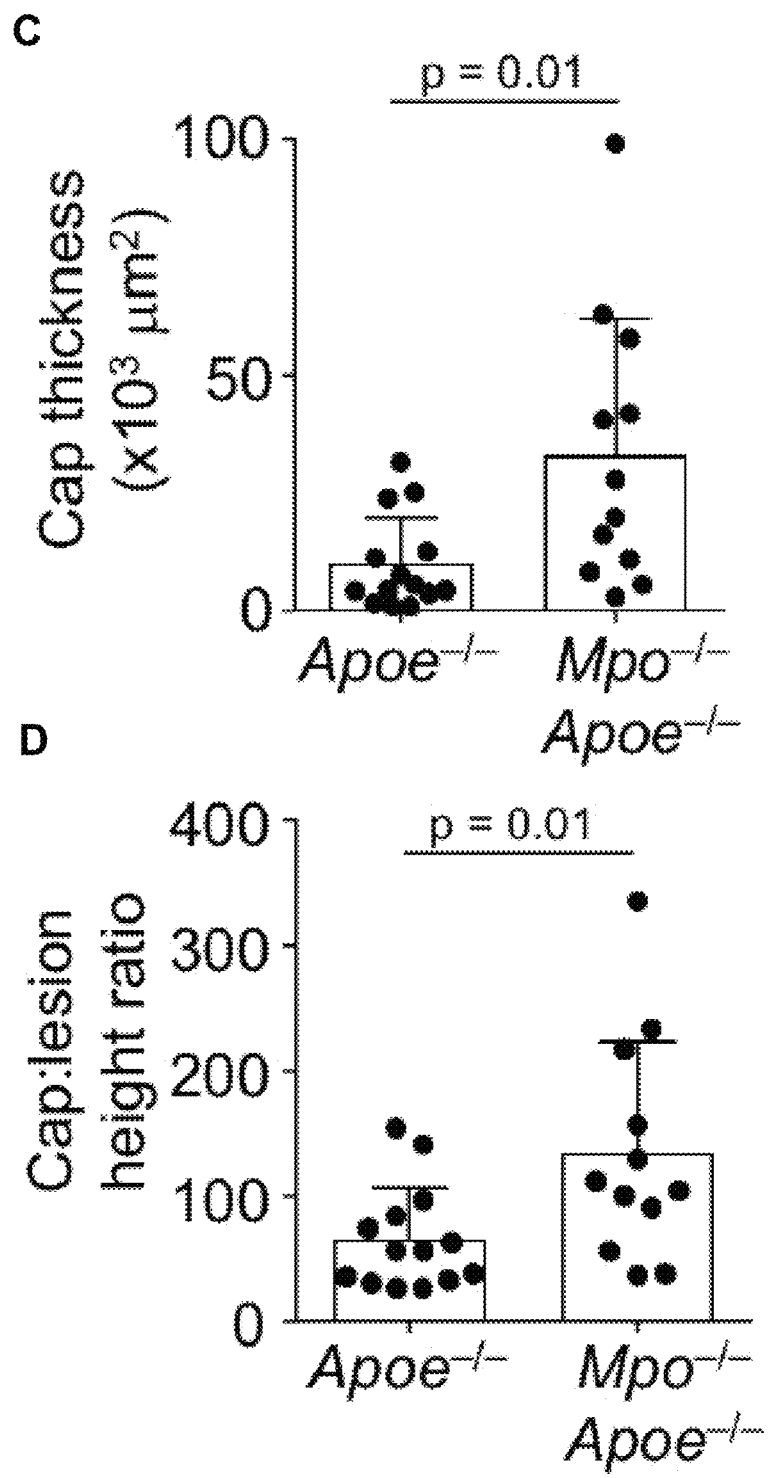

Genetic Deletion of MPO Increases Cap Thickness of Unstable Atherosclerotic Plaque To assess whether MPO contributes to the development of an unstable plaque phenotype, TS surgery was performed in Mpo$^{-/-}$Apoe$^{-/-}$ mice. MPO-Gd MRI in such TS Mpo$^{-/-}$Apoe$^{-/-}$ mice showed attenuated enhancement of the right carotid artery in the region of unstable plaque formation compared with Apoe$^{-/-}$ mice at 60 µmin (FIG. 4A), confirming that activation of this MRI contrast agent is MPO-dependent. Next, fibrous cap thickness, the best morphological discriminator of plaque vulnerability to rupture, was determined. The inventors evaluated the thickness of the cap based on its collagen content determined after staining sections with picrosirius red. The inventors also quantified the cap:lesion height ratio as described in FIG. 1A. Genetic deletion of MPO resulted in a significant 2- and 1.4-fold increase in mean cap thickness and cap:lesion height ratio, respectively, compared with control TS Mpo$^{+/+}$ Apoe$^{-/-}$ mice (FIG. 4B-D), suggesting that MPO plays a role in cap thinning.

Oral Administration of AZM198 Decreases MPO Activity and Increases Cap Thickness in Unstable Atherosclerotic Plaque.

Figure 5:
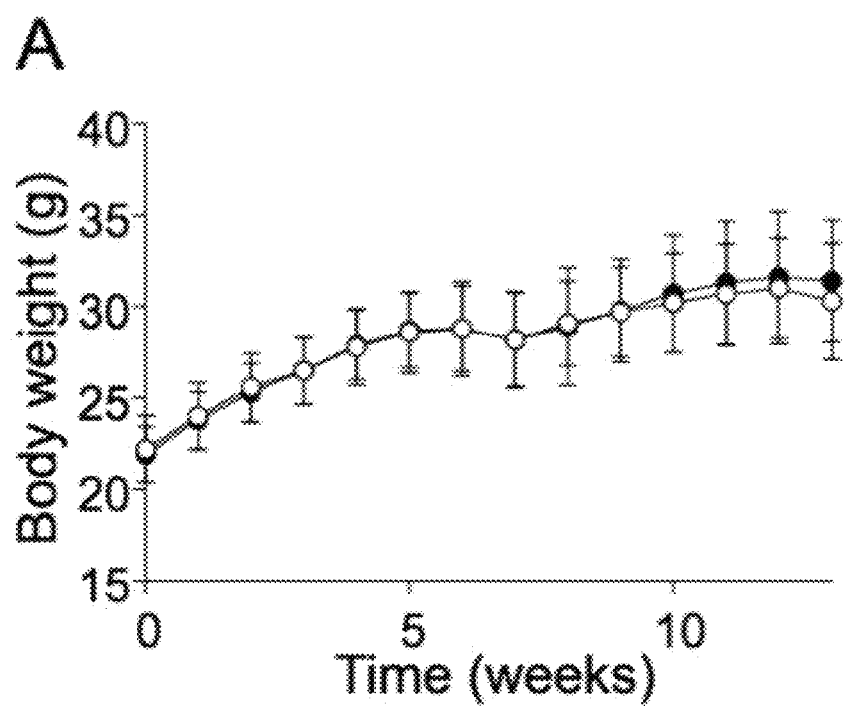
FIG. 5. Effect of AZM198 on body weight of Apoe$^{-/-}$ mice and drug plasma concentration. AZM198 was incorporated into WD provided to the mice (20 g body weight) ad libitum. Assuming a daily food consumption of 3.7 g, the amount of AZM198 consumed corresponded to 500 μmol/kg body weight. A, Body weight of male mice (6 weeks old) receiving WD without (open circles) and with AZM198 (filled circles) for 13 weeks, with TS surgery performed after 6 weeks. Data shown are mean±SEM of n=25 μmice. B, Plasma concentration of AZM198 at the end of the 13 weeks intervention. AZM198 was determined by LC-MS/MS. Data is shown for individual mice as well as mean±SD (n=19).
Figure 5:
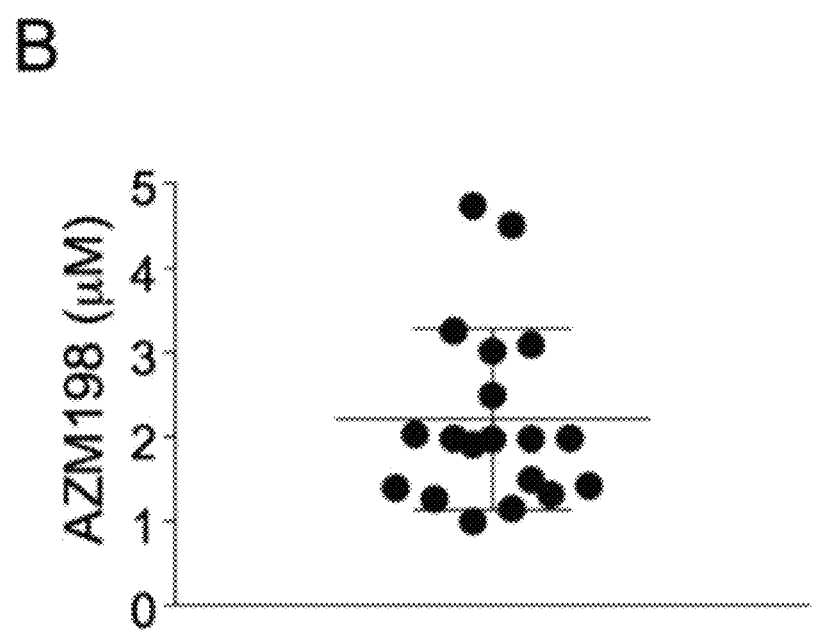
Figure 6:
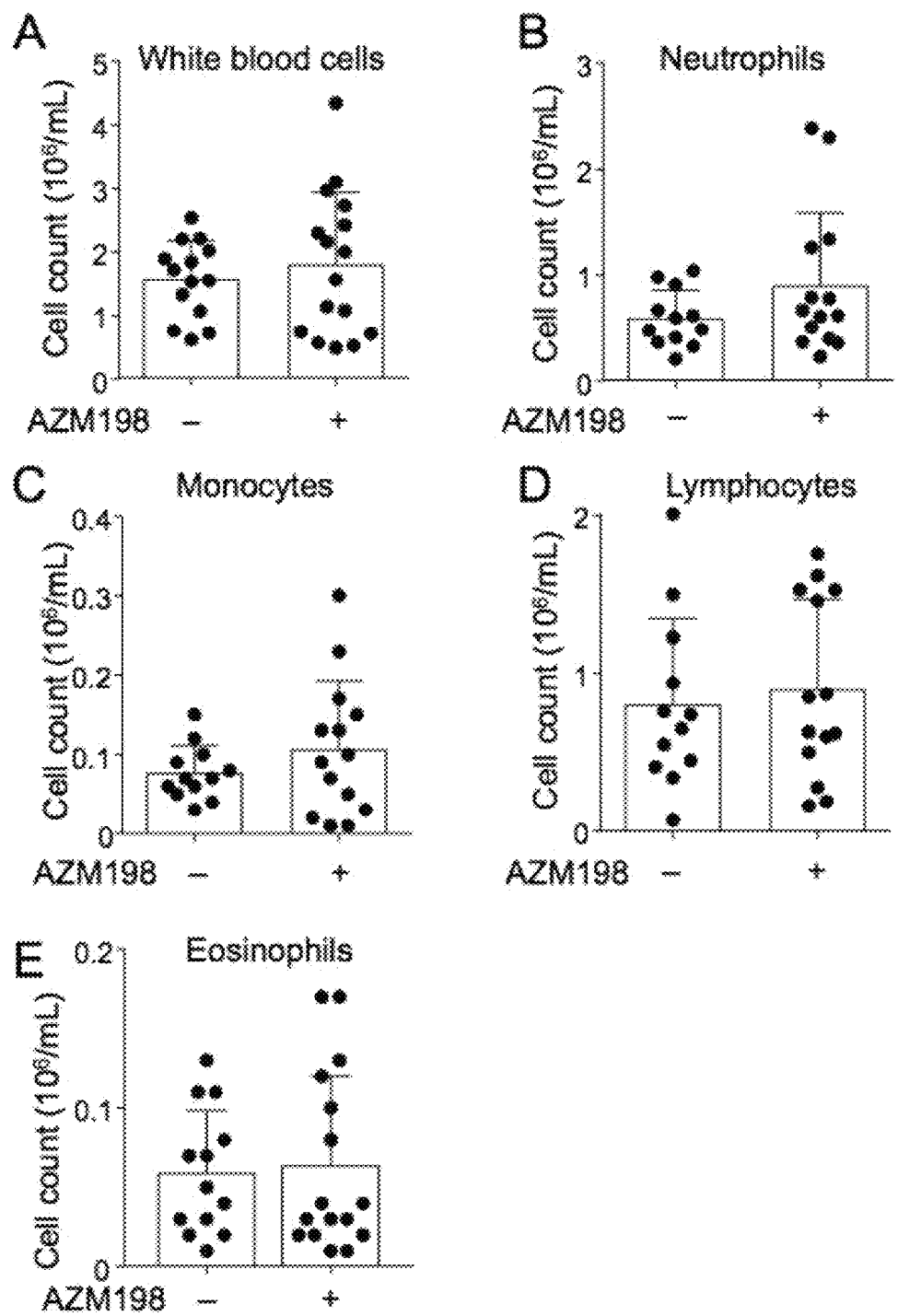
FIG. 6. AZM198 does not affect circulating WBC count. At the end of the 13 weeks intervention, EDTA blood was collected from TS mice fed WD without (−) or with AZM198 (+), and analysed for (A) white blood cell count, (B) neutrophils, (C) monocytes, (D) lymphocytes, and (E)

The inventors investigated if pharmacological inhibition of MPO enzymatic activity increases cap thickness by administering AZM198, a MPO inhibitor with high potency in cell-free MPO activity assays (IC$_{50}$=0.015 µM), to TS Apoe$^{-/-}$ mice. Treatment with AZM198 for the entire 13 weeks duration of intervention had no significant effect on body weight of TS Apoe$^{-/-}$ mice (FIG. 5A), and at termination resulted in a plasma drug concentration of 2.1±0.25 µM (FIG. 5B). This concentration is in the range aimed at and required to inhibit extracellular MPO activity by ~98%. AZM198 had no significant effect on circulating total white blood cell, neutrophil, monocyte, eosinophil or lymphocyte counts (FIG. 6A-E), nor did it affect plasma lipid concentrations (FIG. 7A-D). These results suggest that at the dose used, the MPO inhibitor did not have systemic immune-modulatory or lipid-lowering effects. Importantly, AZM198 decreased in vivo MPO activity in unstable plaque 5-fold compared with corresponding arterial segments in untreated TS Apoe$^{-/-}$ mice (FIG. 8A). AZM198 also significantly decreased MPO activity in unstable plaque assessed ex vivo (FIG. 8B). AZM198 had no significant effect on the arterial concentrations of superoxide radical anion (the immediate precursor of $H_2O_2$), determined in vivo and ex vivo by the conversion of hydroethidine to 2-hydroxyethidium (FIGS. 8C and D). Additionally, AZM198 did not significantly affect the abundance of MPO protein in unstable lesions, as assessed by immunohistochemistry (FIGS. 8E and F). However, AZM198 significantly decreased MPO-Gd-mediated enhancement of unstable plaque compared with controls (ΔCNR 18.7±6.1 vs 6.9±3.1, p=0.03) (FIG. 8G). Together, the data suggest that AZM198 decreases MPO specific activity in unstable plaque.

AZM198 significantly increased cap thickness and cap:lesion height ratio in unstable plaque compared with untreated controls (FIG. 9A-C). Specifically, TS Apoe$^{-/-}$ mice treated with AZM198 had a 65% and 50% increase in fibrous cap thickness and cap:lesion height ratio in stable plaque, respectively, compared with untreated controls (FIGS. 9B and C), without concomitant increases in smooth muscle cells as assessed by smooth muscle actin immunohistochemistry (FIG. 10). Together, these results suggest that inhibiting MPO in TS Apoe$^{-/-}$ mice promotes a more stable plaque phenotype.

Genetic deletion and pharmacological inhibition of MPO decreases fibrin and haemosiderin in unstable atherosclerotic plaque. An increase in atherosclerotic plaque vascularity and proliferation of the adventitial vasa vasorum are markers of atherosclerotic plaque vulnerability, where microrupture and extravasation can cause lesional accumulation of erythrocytes. No immunohistochemical evidence was observed for differences in lesion haemoglobin or Ter119, a marker of red blood cells, between control Apoe$^{-/-}$ and either Mpo$^{-/-}$ Apoe$^{-/-}$ or drug-treated Apoe$^{-/-}$ mice (FIG. 11). However, extravasated haemoglobin is phagocytosed by local macrophages with haemoglobin-derived iron eventually being deposited as haemosiderin. Deletion of the Mpo gene or AZM198 treatment significantly decreased haemosiderin in unstable plaque as assessed by Perl's Prussian Blue staining compared with control Apoe$^{-/-}$ mice (FIGS. 12A and B). Furthermore, deletion of the Mpo gene or AZM198 treatment significantly decreased fibrin in unstable plaque assessed by Martius Scarlett Blue staining compared with control Mpo$^{+/+}$ Apoe$^{-/-}$ mice (FIGS. 12C and D) indicative of reduced fibrin deposition secondary to coagulation and clotting following plaque rupture events. Together, these results suggest that MPO inhibition decreases indicators of intraplaque haemorrhage or prior cap disruption.

As set out in FIG. 14 there is an early increase in ΔCNR after TS surgery of Apoe-mice as assessed by molecular MRI using MPO-Gd. In particular, ΔCNR increases and reaches a maximum as early as 1 week after TS surgery. In FIG. 14, data from the 3 animals undergoing repeated imaging (at 2, 4 and 7 weeks post TS) indicates that the ΔCNR obtained is reproducible within and between individual animals. The pre-contrast ΔCNR values for the 3 μmice undergoing repeated MRI (FIG. 14B) shows comparable low ΔCNR values, demonstrating that the material responsible for the observed enhancement is "washed out"/eliminated from Segment I within a period of <2 weeks. In addition to the observed early increase in ΔCNR obtained 1 week after TS surgery, the data in FIG. 14D show that at that early time point the enhancement is specific for unstable plaque as it is seen only in unstable plaque (UP, Segment I) but not stable plaque (SP, brachiocephalic artery).

AZM198 was administered beginning 1 week after TS surgery (FIG. 14E), that is at a time when ΔCNR in Segment I had reached maximal value. FIG. 14F shows representative pre- and post-contrast (60 μmin) images, showing enhancement in the right carotid artery (Segment I). FIG. 14G shows the CNR time course of control (open circles) and AZM198 treated (filled circles) mice, with AZM198 treatment starting 1 week after TS surgery. The ΔCNR for unstable and stable plaques (UP) of both control and AZM198-treated mice is shown in FIG. 14H and indicates that AZM198 (provided to mice from 1 week after TS surgery onward) significantly decreased enhancement and hence stabilized previously unstable plaque, as assessed by Mann-Whitney test (a non-parametric test was used as the data was not normally distributed as assessed by Shapiro-Wilk).

Discussion

The inventors investigated the role of the inflammatory enzyme MPO in the TS mouse model of atherosclerotic plaque instability. The data show that MPO activity is significantly increased in unstable compared with stable plaque, and that genetic deletion or pharmacological inhibition of MPO increases fibrous cap thickness and decreases markers of intraplaque haemorrhage, indicative of a more stable plaque phenotype. The inventors have also demonstrated that elevated MPO activity in unstable plaque can be detected non-invasively with MPO-Gd MRI and distinguished from stable plaque, highlighting the translational potential of this strategy to improve identification of high-risk disease. These results implicate elevated MPO activity in experimental unstable atherosclerotic plaque and build upon previous clinical studies showing a strong association between circulating or plaque-specific MPO and adverse prognosis.

The inventors used three separate experimental approaches to determine MPO activity. The activatable MRI contrast agent, MPO-Gd, has been used previously in pre-clinical studies to non-invasively demonstrate MPO activity in vivo, including atherosclerotic plaque in the aortic root of Apoe$^{-/-}$ mice. Characterisation of MPO-Gd has established its specificity for MPO. It has been previously reported that formation of 2-chloroethidium from hydroethidine is specific for the MPO-product hypochlorite and has greater sensitivity for MPO activity than measurement of 3-chlorotyrosine for the evaluation of mouse atherosclerotic lesions in vivo and ex vivo. The latter can be explained readily on kinetic grounds. Together, the combination of these distinct experimental approaches provides unambiguous evidence for active MPO being present at elevated levels in unstable compared with stable plaque.

Importantly, the MPO inhibitor, AZM198, had no significant effect on tissue concentrations of 2-hydroxyethidium, a specific oxidation product of superoxide, which in turn is the common precursor of $H_2O_2$. This, together with the absence of overt differences in MPO protein in plaque of drug-treated versus control mice, implies that the observed decrease in MPO activity in drug-treated mice was likely due to a decrease in the specific activity of MPO rather than the availability of its substrate ($H_2O_2$) or expression of MPO protein.

The impact of genetic deletion or pharmacological inhibition of MPO on atherosclerotic plaque characteristics and used fibrous cap thickness as the primary determinant of plaque stability was assessed. This approach has been used previously to demonstrate the plaque-stabilising effect of statins in humans. The data presented demonstrate that genetic deletion of MPO in TS mice results in a doubling of fibrous cap, and that partial inhibition of MPO activity with an MPO inhibitor (AZM198) increased the size of the fibrous cap by ~65%. The comparable extents of benefit observed with MPO deficiency and pharmacological MPO inhibition suggest that the plaque stabilising activity of AZM198 represents an on-target effect.

The observed increase in cap thickness represents a significant shift towards a more stable plaque phenotype. Without wishing to be bound by any specific theory, previous studies have demonstrated that MPO-derived oxidants degrade collagen via activation of latent collagenase and metalloproteinase-7, as well as by inactivation of tissue inhibitor of metalloproteinase-1. Therefore, the increase in collagen content in the fibrous cap produced by genetic or pharmacological blockade of MPO may be due to inhibition of collagen degradation at sites of active inflammation. As humans have five-fold higher neutrophil concentrations, a five-fold higher neutrophil MPO content, and significantly higher concentrations of circulating and plaque-specific MPO, the impact of MPO inhibition on plaque phenotype may be of greater relevance in the clinical setting than in TS mice. Furthermore, as MPO inhibition has been shown to improve myocardial remodelling and function after experimental infarction, this therapeutic strategy may be particularly effective in the secondary prevention setting.

The current study demonstrates that genetic deletion and pharmacological inhibition of MPO significantly decrease plaque fibrin content. This indicates either a reduction in contained plaque rupture events or leakage from neovessels that form a microvascular network throughout unstable atherosclerotic plaque. MPO blockade decreased intraplaque haemosiderin, the long-term storage form of iron derived from erythrocytes/haemoglobin was also observed. Taken together, a reduction in intraplaque fibrin and haemosiderin provides further evidence that inhibition of MPO promotes stabilisation of atherosclerotic plaque.

By investigating the impact of MPO on the development of unstable atherosclerotic plaque phenotypes, the present work significantly differs from previous studies examining the role of MPO on the size of stable atherosclerotic plaque. For example, it has been previously reported that MPO deficiency led to increased lesion size in the aortic root of Ldlr$^{-/-}$ mice, however the presence of MPO activity in such lesions could not be demonstrated. In addition, the data presented herein demonstrate that there is a modest decrease in atherosclerosis lesion size at that site in TS Mpo$^{-/-}$ Apoe$^{-/-}$ compared with TS Apoe$^{-/-}$ mice (FIG. 13A). Therefore, differences in the mouse models used may explain the discordant results. It has been reported that 4-aminobenzoic acid hydrazide (ABAH) decreases atherosclerosis in the aortic root of Apoe$^{-/-}$ mice, whereas the data herein show no significant effect of AZM198 in TS Apoe$^{-/-}$ mice (FIG. 13B). In contrast to AZM198, however, ABAH is unlikely to effectively inhibit MPO activity in vivo. Overall therefore, MPO appears to affect the phenotype rather than the size of atherosclerotic lesions in mouse models of the disease.

The inventors demonstrate that molecular MRI with MPO-Gd can non-invasively discriminate increased MPO activity in unstable plaque and thus is a non-invasive marker of plaque vulnerability. The data herein implicate MPO in fibrous cap thinning and intraplaque haemorrhage, both features of plaque instability, and indicate that MPO is a target for pharmacological intervention. The data also indicate that non-invasive imaging of plaque MPO activity is useful for both the identification of high-risk unstable plaque, and for the evaluation of novel therapies targeting vascular inflammation. This advantageously provides an approach and diagnostic tool to identify and treat subjects at risk of developing acute coronary events.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

What is claimed is:

1. A method for detecting unstable atherosclerotic plaque phenotype in a subject, the method comprising:
   a) administering to the subject a magnetic resonance imaging (MRI) contrast agent capable of being activated by myeloperoxidase (MPO) in atherosclerotic plaque;
   b) allowing the contrast agent to be activated by myeloperoxidase in atherosclerotic plaque;
   c) obtaining an enhanced image of the atherosclerotic plaque from the subject using MRI;
   d) determining from only the enhanced imaging one or more of;
      ΔCNR,
      thickness of a fibrous cap associated with the atherosclerotic plaque; and fibrous cap:lesion ratio,
      wherein a ΔCNR, cap thickness or cap:lesion ratio within a predetermined range indicates that the atherosclerotic plaque has an unstable phenotype.

2. The method according to claim 1, wherein ΔCNR is determined from the enhanced imaging.

3. The method according to claim 1, wherein the predetermined range for ΔCNR is from about 1 to about 80.

4. The method according to claim 3 wherein the predetermined range for ΔCNR is from about 10 to about 30.

5. The method according to claim 1, wherein the predetermined range for cap thickness is from about 0.01 μm to about 65 μm.

6. The method according to claim 1, wherein the predetermined range for cap:lesion ratio is from about 10 to about 20.

7. The method of claim 1, wherein the predetermined range for ΔCNR is from about 10 to about 30, the predetermined range for cap thickness is from about 0.01 μm to about 65 μm, and the predetermined range for cap:lesion ratio is from about 10 to about 20.

8. The method according to claim 1, wherein the MRI contrast agent is a gadolinium(III) chelate.

9. The method according to claim 8, wherein the gadolinium(III) chelate is bis-5HT-DTPA-Gd (MPO-Gd), mono-5HT-DTPA-Gd, bis-o-dianisidine-DTPA-Gd, mono-o-dianisidine-DTPA-Gd, mono-(5-hydroxytryptophan)-DTPA, (mono-HTrp-DTPA), or bis-(5-hydroxytryptophan)-DTPA, (bis-HTrp-DTPA).

10. The method of claim 9, wherein the gadolinium(III) chelate is bis-5HT-DTPA-Gd.

11. The method according to claim 1, further comprising:
   e) administering to a subject identified as having an unstable atherosclerotic plaque phenotype, a therapeutically effective amount of a myeloperoxidase inhibitor to stabilise the unstable atherosclerotic plaque phenotype.

12. The method according to claim 11 wherein the stabilisation of the unstable atherosclerotic plaque phenotype is characterised by at least one of an increase in fibrous cap thickness an improved ΔCNR, and an increase in the cap:lesion ratio.

13. The method according to claim 12 wherein the increase in fibrous cap thickness is at least 50%.

14. The method according to claim 11 wherein the myeloperoxidase inhibitor is AZM198, 3-isobutyl-2-thioxo-7H-purin-6-one, 3-[(4-fluorophenyl)methyl]-2-thioxo-7H-purin-6-one, 3-(tetrahydrofuran-2-ylmethyl)-2-thioxo-7H-purin-6-one, 3-[[(2R)-tetrahydrofuran-2-yl]methyl]-2-thioxo-7H-purin-6-one, and 3-(2methoxyethyl)-2-thioxo-7H-purin-6-one, AZD3241, 2-(6-(5-chloro-2-methoxyphenyl)-4-oxo-2-thioxo-3,4-dihydropyrimidin-1 (2H)-yl) acetamide, or PF-1355.

15. The method according to claim 1, wherein the subject is a human.

* * * * *